(12) United States Patent
Tung

(10) Patent No.: US 8,450,492 B2
(45) Date of Patent: *May 28, 2013

(54) DEUTERATED BENZO[D][1,3]-DIOXOL DERIVATIVES

(75) Inventor: Roger Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 618 days.

This patent is subject to a terminal disclaimer.

(21) Appl. No.: 12/688,466

(22) Filed: Jan. 15, 2010

(65) Prior Publication Data

US 2010/0222589 A1  Sep. 2, 2010

Related U.S. Application Data

(63) Continuation of application No. 11/704,554, filed on Feb. 8, 2007, now Pat. No. 7,678,914, which is a continuation-in-part of application No. 11/498,334, filed on Jul. 31, 2006, now abandoned.

(60) Provisional application No. 60/704,073, filed on Jul. 29, 2005.

(51) Int. Cl.
*C07D 211/22* (2006.01)

(52) U.S. Cl.
USPC .......................................... 546/197; 514/321

(58) Field of Classification Search
USPC ........................................ 514/321; 546/197
See application file for complete search history.

(56) References Cited

U.S. PATENT DOCUMENTS

| | | | |
|---|---|---|---|
| 4,007,196 A | 2/1977 | Christensen et al. | |
| 5,167,948 A * | 12/1992 | Wenzel | 424/1.49 |
| 5,597,826 A | 1/1997 | Howard et al. | |
| 5,874,447 A | 2/1999 | Benneker et al. | |
| 6,221,335 B1 | 4/2001 | Foster | |
| 6,436,938 B1 | 8/2002 | Howard, Jr. | |
| 6,440,710 B1 | 8/2002 | Keinan et al. | |
| 6,603,008 B1 | 8/2003 | Ando et al. | |
| 6,720,003 B2 | 4/2004 | Chen et al. | |
| 7,517,990 B2 | 4/2009 | Ito et al. | |
| 7,678,914 B2 | 3/2010 | Tung | |
| 2002/0013372 A1 | 1/2002 | Ekins | |
| 2007/0082929 A1 | 4/2007 | Gant et al. | |
| 2007/0112031 A1 | 5/2007 | Gant et al. | |
| 2007/0197695 A1 | 8/2007 | Potyen et al. | |
| 2008/0033011 A1 | 2/2008 | Tung | |
| 2008/0103122 A1 | 5/2008 | Veltri | |
| 2009/0143432 A1 * | 6/2009 | Jones et al. | 514/321 |

FOREIGN PATENT DOCUMENTS

| | | |
|---|---|---|
| EP | 0188081 B1 | 3/1992 |
| WO | WO 95/26325 A2 | 10/1995 |
| WO | WO 2007/058998 | 5/2007 |
| WO | WO 2007/118651 A1 | 10/2007 |

OTHER PUBLICATIONS

Heydorn "Paroxetine: a review ..." Exp. Opin. Invest. Drugs vo. 8(4) p. 417-441 (1999).*
Metcalf et al. "Mode of action ..." J. Agr, Food Chem. v.14(6) p. 555-562 (1966).*
Segura et al. "Synthesis of ..." Bioorg. Chem. v.31, p. 248-258 (2003).*
Wade "Deuterium isotope ..." Chemico-Biol. inter. v.117, p. 191-217 (1999).*
Supplementary European Search Report—EP 06813250 Dated Aug. 25, 2010.
Dechant, et al., "Paroxetine a Review of Its Pharmacodynamic and Pharmacokinetic Properties, and Therapeutic Potential in Depressive Illness", Drugs, 1991, vol. 41, pp. 225-253.
Foster, "Deuterium Isotope Effects in the Metabolism of Drugs and Xenobiotics: Implications for Drug Design", Advances in Drug Research, 1985, vol. 14, pp. 1-40.
Haddock, et al., "Metabolic Pathway of Paroxetine in Animals and Man and the Comparative Pharmacological Properties of Its Metabolites", Acta Psychiatrica Scandinavica, 1989, Suppl. 350, pp. 24-26.
U.S. Appl. No. 11/498,334, filed Jul. 31, 2006, Tung.
Fisher, M.B. et al., "Complexities Inherent in Attempts to Decrease Drug Clearance by Blocking Sites of CYP-mediated Metabolism," Current Opinion in Drug Discovery & Development, vol. 9(1), pp. 101-109 (2006).
FDA Center for Drug Evaluation and Drug Research, NDA No. 21-299, Clinical Pharmacology and Biopharmaceutics Review(s), 2003.
Fukuto, J.M. et al., "Determination of the Mechanism of Demethylenation of (Methylenedioxy)phenyl Compounds by Cytochrome P450 Using Deuterium Isotope Effects", J. Med. Chem. 34:2871-2876 (1991).
Kaye, C.M. et al., "A review of the metabolism and pharmacokinetics of paroxetine in man", Acta Psychiatr. Scand. 80(supp. 350):60-75 (1989).
Berteisen, K.M. et al., "Apparent Mechanism-Based Inhibition of Human CYP2D6 In Vitro by Paroxetine: Comparison with Fluoxetine and Quinidine", Drug Metab. Dispos. 31(3):289-293 (2003).
Foster et al., Trends in Pharma. Sci. 1984, 5, 524-527.
Leis et al., J. Mass Spectrom, 2001, 36, 923-928.
Baille T. A., "The Use of Stable Isotopes in Pharmacological Research," Pharmacological Reviews, 33(2): 81-132 (1981).

(Continued)

*Primary Examiner* — Celia Chang
(74) *Attorney, Agent, or Firm* — McCarter & English LLP; Steven G. Davis

(57) ABSTRACT

The present invention relates to an isotopologue of Compound 1 substituted with deuterium at the methylene carbon of the benzodioxol ring. The isotopologues of this invention selective serotonin reuptake inhibitors (SSRIs) and possess unique biopharmaceutical and metabolic properties compared to Compound 1. They may also be used to accurately determine the concentration of Compound 1 in biological fluids and to determine metabolic patterns of Compound 1 and its isotopologues. The invention further provides compositions comprising these deuterated isotopologues and methods of treating diseases and conditions that are responsive to increased neuronal serotonin transmission, alone and in combination with additional agents.

6 Claims, No Drawings

OTHER PUBLICATIONS

Browne, T. R., "Stable Isotope Techniques in Early Drug Development: An Economic Evaluation," J. Clin. Pharmacol., 38: 213-220 (1998).

Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, 14: 653-657 (1987).

Dyck, L. E., et al., "Effects of Deuterium Substitution on the Catabolism of ?—Phenylethylamine: An In Vivo Study," Journal of Neurochemistry, 46(2): 399-404 (1986).

Gouyette, A., "Synthesis of Deuterium-labelled Elliptinium and its Use in Metabolic Studies," Biomedical and Environmental Mass Spectrometry, 15: 243-247 (1988).

Haskins, N. J., "The Application of Stable Isotopes in Biomedical Research," Biomedical Mass Spectrometry, 9(7): 269-277 (1982).

Honma S., et al., "The Metabolism of Roxatidine Acetate Hydrochloride," Drug Metabolism and Disposition, 15(4): 551-559 (1987).

Pieniaszek, H. J., et al., "Moricizine Bioavailability via Simultaneous, Dual, Stable Isotope Administration: Bioequivalence Implications," J. Clin. Pharmacol, 39: 817-825 (1999).

Tonn, G. R., et al., "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes," Biological Mass Spectrometry, 22: 633-642 (1993).

Wolen, R. L., "The Application of Stable Isotopes to Studies of Drug Bioavailability and Bioequivalence," J. Clin. Pharmacol., 26: 419-424 (1986).

Rosel, P., et al., Regional distribution of specific high affinity binding sites for 3H-imipramine and 3H-paroxetine in human brain, J. Neural Trans, 104:89-96 (1997).

Kushner, D.J. et al., "Pharmacological Uses and Perspectives of Heavy Water and Deuterated Compounds," Can. J. Physiol. Pharmacol., 77:79-88 (1999).

CAS RN 533-31-3, Entered Nov. 16, 1984.

* cited by examiner

DEUTERATED BENZO[D][1,3]-DIOXOL DERIVATIVES

CROSS REFERENCE TO RELATED APPLICATIONS

This application is a continuation-in-part of U.S. patent application Ser. No. 11/498,334, filed Jul. 31, 2006, which claims benefit of U.S. provisional application 60/704,073, filed Jul. 29, 2005, the contents of each is incorporated by reference herein.

TECHNICAL FIELD OF THE INVENTION

The present invention relates to novel isotopologues of Compound 1, its acceptable acid with additional deuterium and $^{13}C$ atoms in place of the normally abundant hydrogen and $^{12}C$, respectively addition salts, solvates, hydrates and polymorphs thereof, substituted with deuterium on the methylene carbon atom situated between the oxygens of the benzodioxol ring, and optionally substituted. The compounds of this invention are selective serotonin reuptake inhibitors (SSRIs) and are poorer substrates for metabolism by cytochrome 2D6, and possess unique pharmacokinetic and biopharmaceutical properties compared to the corresponding non-isotopically substituted compounds. The invention also provides compositions comprising a compound of this invention and the use of such compositions in methods of treating diseases and conditions beneficially treated by SSRIs, particularly those relating to major depressive disorder, obsessive compulsive disorder, panic disorder, social anxiety disorder, generalized anxiety disorder, post-traumatic stress disorder, and premenstrual dysphoric disorder. The invention further provides methods for the use of a compound of this invention to determine concentrations of Compound 1, particularly in biological fluids, and to determine metabolism patterns of Compound 1.

BACKGROUND OF THE INVENTION

Compound 1, chemically described variously as (−)-trans-4R-(4'-fluorophenyl)-3S-[(3',4'-methylenedioxyphenoxy)methyl]piperidine; (3S,4R)-3-((benzo[d][1,3]dioxol-5-yloxy)methyl)-4-(4-fluorophenyl)piperidine; trans-(−)-3-[(1,3-benzodioxol-5-yloxy)methyl]-4-(4-fluorophenyl)piperidine, and its pharmaceutically acceptable

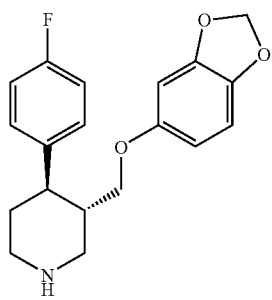

Compound 1 addition salts, hydrates, and polymorphs thereof, are known as a useful selective serotonin reuptake inhibitor (SSRI). This compound and pharmaceutical compositions comprising it have utility in the treatment of depression, obsessive-compulsive disorder, generalized anxiety, post-traumatic stress, major depression, panic disorder, social phobia, premenstrual syndrome, cardiac disorders, non-cardiac chest pain, smoking (both to cause cessation and prevent relapses), reducing platelet activation states, alcoholism and alcohol dependence, psychiatric syndromes (including anger, rejection sensitivity, and lack of mental or physical energy), late luteal phase dysphoric disorder, premature ejaculation, senile dementia, obesity, Parkinson's Disease, and canine affective aggression. See US Food and Drug Administration product label for New Drug Application (NDA) Nos. 020031, 020710, and 020936; Christensen J A and Squires R F, U.S. Pat. No. 4,007,196, to Ferrosan; Lassen J B, U.S. Pat. No. 4,745,122 to Ferrosan; Johnson A M U.S. Pat. No. 5,371,092 to Beecham Group; Crenshaw R T and Wiesner M G, U.S. Pat. No. 5,276,042; Dodman N H, U.S. Pat. Nos. 5,788,986 and 5,554,383 to Trustees of Tufts College; Norden M J U.S. Pat. No. 5,789,449; Gleason M, U.S. Pat. No. 6,121,291 to SmithKline Beecham; Cook L, U.S. Pat. No. 6,071,918 to DuPont Pharmaceuticals; Serebruany V L, U.S. Pat. No. 6,245,782 to Heartdrug Research; Steiner M X, U.S. Pat. No. 6,300,343 to SmithKline Beecham; Krishnan K R et. al., U.S. Pat. No. 6,316,469 to Duke University; Jenner P N, U.S. Pat. No. 6,372,763 to SmithKline Beecham.

Additionally disclosed uses for Compound 1 include methods of inhibiting cancer cell growth, stimulating bone formation by osteoblast stimulation, treatment of dermatological diseases or disorders such as hyperproliferative or inflammatory skin diseases, and treatment of premature female orgasm: see US Patent Applications 20040127573 (Telerman A et. al.); 20040127573 (Stashenko P and Battaglino R); 20050013853 and 20040029860 (Gil-Ad I and Weizman A); and 20050054688 (May K E and Quinn P).

Definitions and descriptions of these conditions are known to the skilled practitioner and are further delineated, for instance, in the above patents and patent applications and references contained therein. See also: Harrison's Principles of Internal Medicine 16th Edition, Kasper D L et. al. Eds., 2004, McGraw-Hill Professional; and Robbins & Cotran Pathologic Basis of Disease, Kumar V et. al. Eds., 2004, W.B. Saunders.

The combination of Compound 1 with additional agents extends or enhances its utility in the treatment or prevention of depression, hypertension, generalized anxiety disorder, phobias, posttraumatic stress syndrome, avoidant personality disorder, sexual dysfunction, eating disorders (including bulimia, anorexia nervosa, and binge eating), obesity, chemical dependencies, cluster headache, migraine, pain (including neuropathic pain, diabetic nephropathy, post-operative pain, psychogenic pain disorders, and chronic pain syndrome), Alzheimer's disease, obsessive-compulsive disorder, panic disorder with or without agoraphobia, memory disorders, Parkinson's diseases, endocrine disorders, vasospasm, cerebellar ataxia, gastrointestinal tract disorders, negative symptoms of schizophrenia, premenstrual syndrome, Fibromyalgia Syndrome, urinary incontinence (including stress incontinence), Tourette's syndrome, trichotillomania, kleptomania, male impotence, cancer, chronic paroxysmal hemicrania and headache in a mammal, sleep-related breathing disorders, cognitive deficits due to aging, stroke, head trauma, neurodegenerative diseases, schizophrenia, anxiety, aggression, stress, disorders of thermoregulation, respiratory disease, bipolar disorder, psychosis, sleep disorders, mania (including acute mania), bladder disorder, genitourinary disorder, cough, emesis, nausea, psychotic disorders such as paranoia and manic-depressive illness, tic disorder, diabetic cardiomyopathy, diabetic retinopathy, cataracts, myocardial infarction, prolonged fatigue, chronic fatigue, chronic fatigue syndrome, premature ejaculation, dysphoria, post partum depression, social phobia, disruptive behavior disorders, impulse control disorders, borderline personality disorder, attention deficit disorders without hyperactivity, Shy-Drager Syndrome, cerebral ischemia, spinal cord trauma, Huntington's Chorea, amyotrophic lateral sclerosis, AIDS-induced dementia, muscular spasms, convulsions, perinatal hypoxia, hypoxia, cardiac arrest, hypoglycemic neuronal damage, ocular damage and retinopathy, brain edema, tardive dyskinesia, cerebral deficits subsequent to cardiac bypass surgery and grafting, affective disorders, mood disorders, agoraphobia without history of panic disorder, and acute stress disorders. These additional agents are also useful for reducing the side effects of Compound 1, enhancing or potentiating its activity, or increasing its duration of pharmacological action. U.S. Pat. No. 5,776,969 (James S P) to Eli Lilly; U.S. Pat. No. 5,877,171 (McLeod M N); U.S. Pat. No. 5,977,099 (Nickolson V J) to Akzo Nobel; U.S. Pat. Nos. 5,962,514 and 6,169,098 (Evenden J and Thorberg S-O) to Astra; U.S. Pat. No. 5,958,429 (Wong D T) to Eli Lilly; U.S. Pat. No. 5,945,416 (Shannon H E and Womer D E) to Eli Lilly; U.S. Pat. No. 6,066,643 (Perry K W) to Eli Lilly; U.S. Pat. Nos. 5,817,665 and 6,034,091 (Dante L G) to Nagle J S; U.S. Pat. No. 5,990,159 (Meulemans A L G et. al.) to Janssen Pharmaceutica; U.S. Pat. No. 6,001,848 (Noble E P) to The Regents of the University of California; U.S. Pat. No. 6,011,054 (Oxenkrug G F and Requintina P J) to St. Elizabeth's Medical Center of Boston; U.S. Pat. No. 6,080,736 (Landry D W and Klein D F) to Janus Pharmaceuticals; U.S. Pat. No. 6,162,805 (Hefti F F) to Merck Sharp & Dohme; U.S. Pat. No. 6,136,861 (Chenard B L) to Pfizer; U.S. Pat. No. 6,147,072 (Bymaster F P et. al.) to Eli Lilly; U.S. Pat. No. 6,218,395 (Swartz C M); U.S. Pat. No. 6,169,105 (Wong D T and Oguiza J I) to Eli Lilly; U.S. Pat. No. 6,191,133 (Coppen A J) to Scarista; U.S. Pat. Nos. 6,239,126 and 6,242,448 (Kelly M G et. al.) to American Home Products; 6,372,919 (Lippa A S and Epstein J W) to DOV; U.S. Pat. No. 6,369,051 (Jenkins S N) to American Home Products; U.S. Pat. No. 6,358,944 (Lederman S et. al.) to Vela Pharmaceuticals; U.S. Pat. Nos. 6,121,259; 6,174,882; 6,348,455; 6,352,984; and 6,468,997 (Yelle W E) to Sepracor; U.S. Pat. No. 6,403,597 (Wilson L F et. al.) to Vivus; U.S. Pat. Nos. 6,395,788 and 6,541,523 (Iglehart I W III) to Vela Pharmaceuticals; U.S. Pat. Nos. 6,127,385 and 6,395,752 (Midha K K et. al.) to Pharmaquest Limited; 6,380,200 (Mylari B L) to Pfizer; U.S. Pat. No. 6,387,956 (Shapira N A et. al.) to University of Cincinnati; U.S. Pat. No. 6,444,665 (Helton D R et. al.) to Eli Lilly; U.S. Pat. No. 6,541,478 (O'Malley S et. al.) to Yale University; U.S. Pat. No. 6,541,043 (Lang P C) to DexGen Pharmaceuticals; U.S. Pat. No. 6,562,813 (Howard H R) to Pfizer; U.S. Pat. No. 6,579,899 (Wurtman J J and Wurtman R J) to Massachusetts Institute of Technology; U.S. Pat. No. 6,627,653 (Plata-Salaman C R et. al.) to Ortho-McNeil; 6,649,614 (Carlson E J and Rupniak N M) to Merck Sharp & Dohme; U.S. Pat. No. 6,667,329 (Maj J) to Boehringer Ingelheim; U.S. Pat. No. 6,727,242 (Radulovacki M and Carley D W) to The Board of Trustees of the University of Illinois; U.S. Pat. Nos. 6,656,951; 6,780,860; 6,815,448; 6,821,981; and 6,861,427 (Stack; Gary P et. al.) to Wyeth; U.S. Pat. No. 6,878,732 (Wrobleski M L) to Schering Corporation; and U.S. Pat. No. 6,894,053 (Childers W E et. al.) to Wyeth.

Further disclosed are additional combinations of Compound 1 with other agents extending or enhancing its utility in the treatment or prevention of autism, dyskinesia, disthymic disorder; obesity due to genetic or environmental causes; polycystic ovary disease, craniopharyngeoma, Prader-Willi Syndrome, Frohlich's Syndrome, Type II diabetes, growth hormone deficiency, Turner's Syndrome; pro-inflammatory cytokine secretion or production, jet lag, insomnia, hypersomnia, nocturnal enuresis, restless-legs syndrome, vaso-occlusive events, hyperglycemia, hyperinsulinaemia, hyperlipidaemia, hypertriglyceridemia, diabetes, insulin resistance, impaired glucose metabolism, conditions of impaired glucose tolerance (IGT), conditions of impaired fasting plasma glucose, glomerulosclerosis, syndrome X, coronary heart disease, angina pectoris, vascular restenosis, endothelial dysfunction, impaired vascular compliance, or congestive heart failure; or to increase the onset of action of Compound 1. US Patent Applications 20020032197, 20020002137, 20020086865, 20020077323, 20020103249, 20020094960, 20030109544, 20030092770, 20030144270, 20030158173, 20030139395, 20030055070, 20030139429, 20040044005, 20010014678, 20040044005, 20030235631, 20030027817, 20030229001, 20030212060, 20040132797, 20040204469, 20040204401, 20040171664, 20040229940, 20040229941, 20040229942, 20040229911, 20040224943, 20040229866, 20040224942, 20040220153, 20040229849, 20050069596, 20050059654, 20050014848, 20050026915, 20050026946, 20050143350, 20020035105, 20050143314, 20050137208, 20040010035, 20040013741, 20050136127, 20050119248, 20050119160, 20050085477, 20050085475, 20010003749, 20050009815, 20040248956, 20050014786, 20050009870, 20050054659, 20050143381, 20050080087, 20050070577, and 20050080084.

Compound 1 has been characterized by in vitro studies of binding to rat cortical membranes, wherein radiolabeled Compound 1 was found to bind to a single, high affinity, saturable site. See e.g. Habert E et. al., Eur. J. Pharmacol. 1985 118: 107.

Compound 1 has also been characterized in a number of animal model systems. For instance, in models of depression, obesity, and anxiety, treatment with Compound 1 accurately produced results that are correlated with human clinical effects. See, e.g. Akegawa Y et. al. Methods Find Exp Clin Pharmacol 1999 21: 599; Lassen J B, U.S. Pat. No. 4,745,122 to Ferrosan; and Hascoet M et. al., Pharmacol. Biochem. Behav. 2000 65: 339.

In human clinical studies, Compound 1 demonstrated good tolerability and statistical efficacy in patients suffering from major depression, minor depression and dysthymia, obsessive-compulsive disorder, panic disorder, social anxiety disorder, generalized anxiety disorder, and post-traumatic stress disorder. Compound 1 is highly effective, for instance demonstrating superior antidepressant effects to other compounds with the same mechanism of action in a number of direct comparison studies. See, e.g. US Food and Drug Administration product label for New Drug Application (NDA) Nos. 020031, 020710, and 020936; Wagstaff A J et. al., Drugs 2002 62: 655; Katona C and Livingston G, J. Affect. Disord. 2002 69: 47.

Following oral administration to humans, Compound 1 is well absorbed, after which it undergoes extensive oxidative and phase II metabolism. Its major metabolic pathway proceeds by oxidative cleavage of the benzodioxol ring to forming a catechol metabolite. Subsequent phase II metabolism involves mainly methylation, glucuronidation and sulfation. See Scheme I. In vitro measurements indicate that these metabolites possess <2% of the potency of Compound 1 and therefore do not contribute pharmacodynamically to its action. During a 10-day post-dosing period following a 30 mg oral solution dose of radiolabeled Compound 1 in healthy volunteers, approximately 64% of Compound 1 was found to be excreted in the urine, comprising 2% as the parent compound and 62% as metabolites. About 36% was excreted in the feces, mostly as metabolites and less than 1% as the parent compound during this period. US FDA approved label for NDA # 020031, approved Jan. 12, 2005.

The benzodioxol ring scission is carried out in significant part by cytochrome 2D6 (CYP2D6), which acts as a high affinity, but relatively low capacity, oxidant. Compound 1 also acts as a highly potent, mechanism based inactivator of CYP2D6, possibly through formation of a carbene intermediate during the metabolic oxidation step or by formation of an ortho-quinone and subsequent reaction with active-site nucleophiles. Bertelsen K M et. al., Drug Metab. Dispos. 2003 31: 289; Murray M, Curr. Drug Metab. 2000 1: 67; Ortiz de Montellano and Correi M A in "*Cytochrome P450 Structure, Mechanism and Biochemistry*" (Ortiz de Montellano P R ed) pp 305-366, 1995 Plenum Press, New York; Wu et. al., Biochem. Pharmacol. 1997 53: 1605; Bolton J L et. al., 1994 Chem. Res. Toxicol. 7: 443.

Clinically, this mechanism-based inactivation manifests in several ways. For instance, Compound 1 displays significantly non-linearity pharmacokinetics, with steady state doses several times the levels expected from a single dose as a result of auto-inhibition of its metabolism. Compound 1 also causes a dose-dependent, highly significant reduction in CYP2D6 activity. CYP2D6 comprises the main metabolic pathway for a number of other clinically important drugs, including for instance anti-cancer agents, other anti-depressants, and antipsychotics; as well as drugs of abuse such as the widely used drug "Ecstasy". Co-dosing Compound 1 with those agents causes clinically significant increases in their blood levels, leading to the potential for increased toxicity. Jeppesen U et. al., Eur. J. Clin. Pharmacol. 1996 51: 73; US FDA approved label for NDA # 020935, approved Jan. 12, 2005; Laugesen S et. al., Clin Pharmacol Ther. 2005 77: 312; Jin Y et. al., J. Natl. Cancer Inst. 2005 97: 30; Joos A A B et al., Pharmacopsychiat. 1997 30, 266; Segura M et. al., Clin Pharmacokinet. 2005 44: 649.

Compound 1 is subject to substantial inter-patient variation. Patients possessing relatively low and relatively high levels of CYP2D6 activity have been shown to metabolize Compound 1 at substantially different rates, leading to an approximately 3-fold longer half-life in a European cohort of poor metabolizers (PMs) with low CYP2D6-mediated oxidative efficiency versus extensive metabolizers (EMs) with higher CYP2D6 activity; Sindrup S H et. al., Clin. Pharmacol. 1992 51: 278. Even when measured at steady state, at which time variability is substantially less than on initial dosing, high variability of Compound 1 was observed in a test population (about 30-70% coefficients of variability across maximal and minimal plasma concentrations (Cmax and Cmin) and overall exposure measured as area under the plasma concentration-time curve ($AUC_\infty$)). Kaye C M et. al., Acta Psychiatr. Scand. 80 (Suppl. 350): 60.

CYP2D6 is the source of substantial variability in the pharmacokinetics of a number of drugs due to well-known polymorphisms resulting in low CYP2D6 activity in a substantial percentage of the population, including about 2% of Asians and 7-8% of Caucasians (Wolf C R and Smith G, IARC Sci. Publ. 1999 148: 209 (chapter 18); Mura C et. al., Br. J. Clin. Pharmacol. 1993 35: 161; Shimizu T et. al., Drug Metab. Pharmacokinet. 2003 18: 48). Notably, different CYP2D6 polymorphisms exist across racial types, and it is possible that the even greater variability may exist in other patient populations with different pharmacogenomic backgrounds. Shimada T et. al., Pharmacogenetics 2001 11: 143.

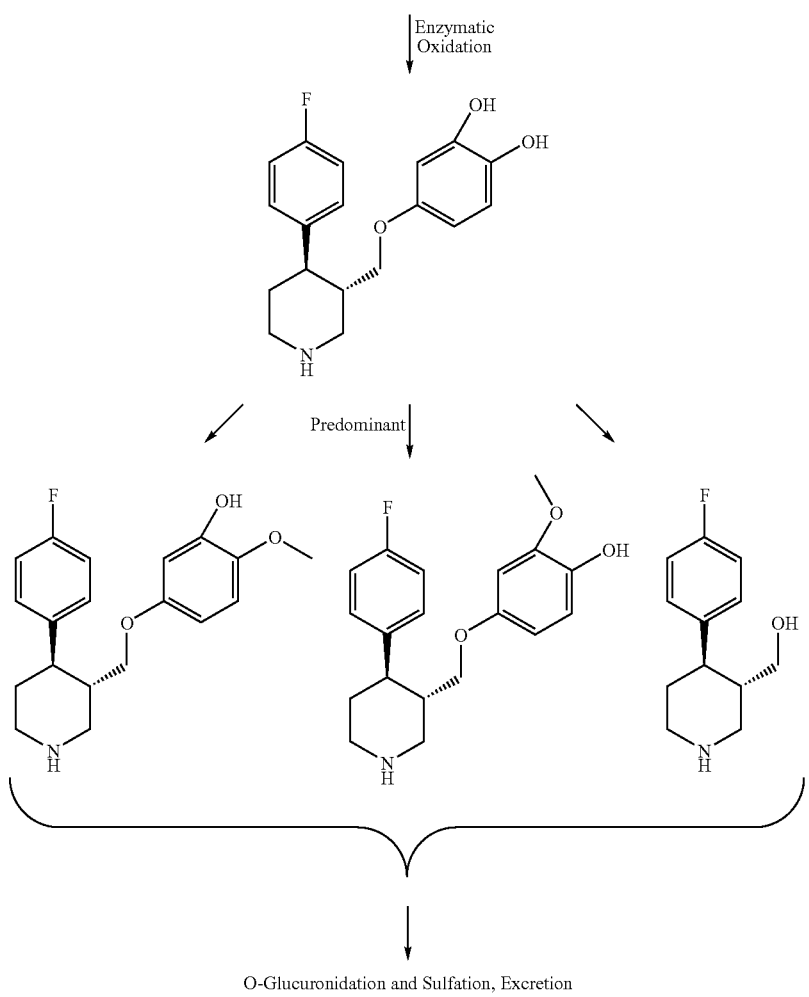

Scheme I

Compound 1

It is therefore desirable to create a compound displaying the beneficial activities of Compound 1, but with a decreased metabolic liability for CYP2D6, to further extend its pharmacological effective life in extensive metabolizers, decrease population pharmacokinetic variability and/or decrease its potential for dangerous drug-drug interactions.

SUMMARY OF THE INVENTION

The present invention solves the problems set forth above by providing an isolated compound of Formula I:

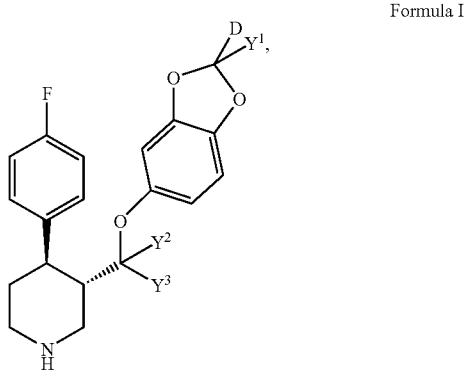

Formula I or a salt thereof; or a prodrug, or a salt of a prodrug thereof; or a hydrate, solvate, or polymorph thereof; wherein:
 D is deuterium;
 each Y is independently selected from deuterium or hydrogen;
 each hydrogen is independently optionally replaced with deuterium; and
 each carbon is independently optionally replaced with $^{13}C$.

A compound of Formula I reduces the efficiency of benzodioxol ring cleavage by CY2D6 and beneficially decreases the rate of mechanism-based CYP2D6 inhibition relative to Compound 1. This beneficially decreases the rates of clearance as compared to Compound 1 and produces a corresponding increase in pharmacokinetic half-life.

The decreased CYP2D6 inhibition is important in reducing the pharmacokinetic interactions between Compound 1 and other drugs metabolized by that enzyme. This provides increased safety as compared to Compound 1.

In particular, this would produce benefits in the treatment of co-morbidities and the use of combinations of medications, which is common in patients suffering from depression, anxiety and other psychiatric disorders. Moreover, it would be useful in patients taking Compound 1, while being treated by different healthcare providers without disclosing all of their medications to each of them. It would also be beneficial in patients who are using drugs of abuse while taking Compound 1 without the knowledge of their physician.

The decreased substrate efficiency for CYP2D6 at the methylenedioxy portion of the benzodioxol ring demonstrated by the compounds of this invention will provide the further benefit of reducing inter-patient pharmacokinetic variability observed for Compound 1.

The compounds of the present invention comprising additional deuterium for hydrogen replacement at the methylenedioxy carbon demonstrate the added benefit of reduced metabolism by other cytochrome P450 enzymes. This is important for poor metabolizers of Compound 1, wherein the main metabolic pattern of Compound 1 proceeds largely by scission of the benzodioxol ring, likely due to oxidative attack by another cytochrome enzyme. Also, a relatively minor amount of ring scission (complete cleavage of the benzodioxol ring, forming 4-(4-fluorophenyl)-3-hydroxymethylpiperidine) observed in normal metabolizers, which could result from oxidation of the methylene carbon attached to the piperidine ring, may become more predominant if the benzodioxol ring is metabolically stabilized. Therefore, compounds of this invention that are deuterated at that carbon will also be beneficial to the clearance rate of the compound.

The compounds of this invention, and compositions comprising them, are useful for treating or lessening the severity of disorders characterized by reduced serotonin-dependent neurological activity. Preferred applications for compounds of formula I include methods of use in treating depression, anxiety, stress, phobias, panic, dysphoria, and other psychiatric disorders, and pain.

The compounds and compositions of this invention are also useful as analytical reagents for determining the concentration of the Compound 1 in solution. "Compound 1" as used herein refers to a compound wherein all hydrogen and all carbon atoms are present at their natural isotopic abundance percentages. It is recognized that some variation of natural isotopic abundance occurs depending upon the origin of chemical materials. The concentration of naturally abundant stable hydrogen and carbon isotopes, notwithstanding this variation, is small and immaterial with respect to the degree of stable isotopic substitution of compounds of this invention. See for instance Wada E and Hanba Y, Seikagaku 1994 66: 15; Ganes L Z et. al., Comp. Biochem. Physiol. A Mol. Integr. Physiol. 1998 119: 725.

Incorporation of deuterium in place of hydrogen is known in certain instances to have significant effects on the physiological and pharmacological activities of the substituted compound. For instance, N-nitrosamines substituted with deuterium can display increased, decreased, or unchanged carcinogenicity depending on where in the compound hydrogen is replaced with deuterium and on the identity of the compound to which substitutions are made (Lijinsky W et. al., Food Cosmet. Toxicol. 1982 20: 393; Lijinsky W et. al., JCNI 1982 69: 1127). Similarly, both increases and decreases in bacterial mutagenicity of deuterium-substituted aza-amino acids are known, depending on the identity of the amino acid derivative and position of substitution (Mangold J B et. al., Mutation Res. 1994 308: 33). Reduced hepatotoxicity of certain deuterium-substituted compounds is known (Gordon W P et. al., Drug Metab. Dispos. 1987 15: 589; Thompson D C et. al., Chem. Biol. Interact. 1996 101:1). Deuterium substitution can affect compound's odors (Turin L, Chem. Senses 1996 21: 773) and plasma protein binding (Echmann M L et. al., J. Pharm. Sci. 1962 51: 66; Chemah Y. et. al., Biomed. Environm. Mass Spectrom. 1987 14: 653; Chemah Y. et. al., Biochem. Pharmacol. 1988 37: 1311). Changes in the biodistribution and clearance of certain deuterium-substituted compounds suggests changes in their recognition by active transport mechanisms (Zello G A et. al., Metabolism 1994 43: 487; Gately S J et. al., J. Nucl. Med. 1986 27: 388; Wade D, Chem. Biol. Interact. 1999 117: 191).

Replacement of hydrogen with deuterium at sites subject to oxidative metabolism by, for instance, heme proteins such as cytochrome P450 and peroxidase enzymes, is known in certain, but not all, cases to produce a significant reduction in the rate of metabolism due to the primary isotope effect of breaking the C-$^1$H versus C-$^2$H bond (see, e.g., Guengerich F P et. al., J. Biol. Chem. 2002 277: 33711; Kraus, J A and Guengerich, F P, J. Biol. Chem. 2005 280: 19496; Mitchell K H et. al., Proc. Natl. Acad. Sci. USA 2003 109: 3784; Nelson S D and Trager W F, Drug Metab. Dispos. 2003 31: 1481; Hall L R and Hanzlik R P, J. Biol. Chem. 1990 265: 12349; Okazaki O and Guengerich F P, J. Biol. Chem. 268, 1546; Iwamura S et. al., J. Pharmacobio-Dyn. 1987 10: 229). If the C—H bond breaking step is rate-limiting, a substantial isotope effect can be observed. If other steps determine the overall rate of reaction, the isotope effect may be insubstantial. In cases where a rate-limiting step of a reaction involves rehybridization of the attached carbon from sp2 to sp3, deuterium substitution often creates a negative isotope effect, speeding up the reaction rate. Introducing deuterium into a compound at a site subject to enzymatic oxidation does not predictably produce a significant pharmacokinetic change. See for instance Mamada K et. al., Drug Metab. Dispos. 1986 14: 509; Streeter A J et. al., Arch. Toxicol. 1990 64: 109; Morgan D S et. al., Int. Arch. Occup. Environ. Health 1993 65 (1 Suppl.): S139.

Although incorporation of deuterium into specific organic compounds can change their pharmacological properties, general exposure to and incorporation of deuterium is safe within levels potentially achieved by use of compounds of this invention as medicaments. For instance, the weight percentage of hydrogen in a mammal (approximately 9-10%) and natural abundance of deuterium (approximately 0.015%) indicates, for instance that an average adult US male normally contains approximately 1.2 grams of deuterium (see e.g. Harper V W et. al. "Review of Physiological Chemistry" 16$^{th}$ Edition, 1977 Lange Medical Publications; Ogden C L et. al. CDC Adv. Data 2004 347: 1; www.cdc.gov/nchs/data/ad/ad347.pdf).

Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. N.Y. Acad. Sci. 1960 84: 736; Czakja D M et. al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et. al. in "*Dosimetry & Treatment Planning for Neutron Capture Therapy*", Zamenhof R, Solares G and Harling O Eds. 1994. Advanced Medical Publishing, Madison Wis. pp. 125-134.). These authors report a clinical protocol in their practice involving oral administration of up to 1 liter per day of deuterated water ($D_2O$) for up to 5 days, followed by intravenous administration of 4 liters of deuterated water prior to radiation procedures; this deuterated water is readily incorporated throughout the body beyond the fluid compartment, including in glucose and glycogen, fats, and cholesterol and thus cell walls (e.g. see Diabetes Metab. 1997 23: 251).

In a 70 kg human, 15% replacement of the hydrogen in the fluid compartment with deuterium corresponds to incorporation of approximately 1 kg of deuterium or the equivalent of approximately 5 kg of deuterated water. These quantities are orders of magnitude beyond the conceived level of administration of any of the deuterium-containing compounds of this invention.

Deuterium tracers including as deuterium-labeled drugs and doses, in some cases repeatedly, of thousands to tens of thousands of milligrams of deuterated water, are also used in healthy humans of all ages including neonates and pregnant women, without reported incident (e.g. Pons G and Rey E, Pediatrics 1999 104: 633; Coward W A et. al., Lancet 1979 7: 13; Schwarcz H P, Control. Clin. Trials 1984 5 (4 Suppl): 573; Eckhardt C L et. al. Obes. Res. 2003 11: 1553; Rodewald L E et. al., J. Pediatr. 1989 114: 885; Butte N F et. al., Br. J. Nutr. 1991 65: 3; MacLennan A H et. al., Am. J. Obstet. Gynecol. 1981 139: 948). Thus, it is clear that any deuterium released, for instance during the metabolism of compounds of this invention, poses no health risk.

The compounds of this invention display decreased mechanism-based inactivation of CYP2D6 than Compound 1 and therefore display a reduced rate of oxidative metabolism and decreased mechanism-based inactivation of CYP2D6. This reduces the extent of undesirable metabolic drug-drug interactions observed with Compound 1, reducing the need for dose adjustments of other drugs taken by patients treated with these agents.

The altered properties of the compounds of this invention will not obliterate their ability to bind to their protein target. This is because such binding is primarily dependent upon non-covalent binding between the protein and the inhibitor which may be impacted both positively and negatively by isotopic substitution, depending on the specific substitution involved, and any negative effects that a heavy atom of this invention may have on the highly optimized non-covalent binding between compounds of formula I and serotonin uptake proteins will be relatively minor. Major factors contributing to the noncovalent recognition of small molecules by proteins and the binding strength between them include: Van der Waals forces, hydrogen bonds, ionic bonds, molecular reorganization, desolvation energy of the small molecule, hydrophobic interactions and, in certain instances, displacement energy for pre-existing bound ligands. See, for instance, Goodman & Gilman's *The Pharmacological Basis of Therapeutics*, Tenth Edition, Hardman J G and Limbird L E, eds. McGraw-Hill, 2001 and *The Organic Chemistry of Drug Design and Drug Action*, Silverman R B, 2004, Academic Press.

The compounds of this invention possess molecular topology that is very similar to Compound 1, since exchange of deuterium for hydrogen does not alter molecular shape and exchange of $^{13}C$ for $^{12}C$ is conformationally neutral (Holtzer M E et. al., Biophys. J. 2001 80: 939). Deuterium replacement does cause a slight decrease in Van der Waals radius (Wade D, Chem. Biol. Interact. 1999 117: 191); but applicant believes that such decrease will not greatly reduce binding affinity between the molecule and its receptor. Furthermore, the slightly smaller size of the deuterated compounds of this invention prevents their being involved in new undesirable steric clashes with the binding protein relative to the Compound 1.

Neither deuterium nor $^{13}C$ atoms in the compounds of this invention contribute significantly to hydrogen bonding or ionic interactions with the protein receptors. This is because the major hydrogen bond and ionic interactions formed by Compound 1 with serotonin uptake proteins are mediated by the oxygens, nitrogens, and the amine-bound hydrogens within Compound 1. Any deuterium atoms attached to the amine nitrogen will be rapidly exchanged with bulk solvent protons under physiological conditions. Protein reorganization or side chain movement will be identical between a compound of this invention and Compound 1. Desolvation energy of a compound of this invention will be equivalent to or less than that of Compound 1, resulting in neutral or increased binding affinity for the receptor; Turowski M et. al., J. Am. Chem. Soc. 2003 125: 13836. The replacement of $^{13}C$ in place of $^{12}C$ in compounds of this invention will have no practical change in desolvation.

Thus, a compound of this invention advantageously retains substantial binding to serotonin uptake proteins and is an active inhibitor of serotonin uptake.

DETAILED DESCRIPTION OF THE INVENTION

The present invention provides an isolated compound of formula I:

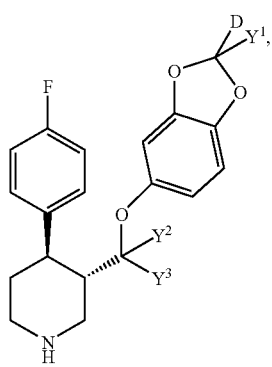

or a salt thereof; or a prodrug, or a salt of a prodrug thereof; or a hydrate, solvate, or polymorph thereof; wherein:

D is deuterium;

each Y (e.g., $Y^1$, $Y^2$, $Y^3$) is independently selected from deuterium or hydrogen;

each hydrogen is optionally replaced with deuterium; and each carbon is optionally replaced with $^{13}C$.

According to a preferred embodiment, $Y^1$ is deuterium.

According to another preferred embodiment, at least one of $Y^2$ and $Y^3$ is independently deuterium. More preferably, both $Y^2$ and $Y^3$ are deuterium.

In another preferred embodiment, each of $Y^1$, $Y^2$ and $Y^3$ is deuterium.

In yet another preferred embodiment, each hydrogen atom on the fluorophenyl ring is replaced with deuterium.

The term "compound" as used herein, is intended to include salts, prodrugs, and prodrug salts of a compound of formula I. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —$NO_2$, —ONO, or —$ONO_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines.

A prodrug salt is a compound formed between an acid and a basic group of the prodrug, such as an amino functional group, or a base and an acidic group of the prodrug, such as a carboxyl functional group. In a preferred embodiment, the prodrug salt is a pharmaceutically acceptable salt. According to another preferred embodiment, the counterion to the saltable prodrug of the compound of formula I is pharmaceutically acceptable. Pharmaceutically acceptable counterions include, for instance, those acids and bases noted herein as being suitable to form pharmaceutically acceptable salts.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-to 1 uenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyl rate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromlc acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates and solubility (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The compounds of the present invention contain one or more asymmetric carbon atoms. As such, a compound of this invention can exist as the individual stereoisomers (enantiomers or diastereomers) as well a mixture of stereoisomers. Accordingly, a compound of the present invention will include not only a stereoisomeric mixture, but also individual respective stereoisomers substantially free from one another stereoisomers. The term "substantially free" as used herein means less than 25% of other stereoisomers, preferably less than 10% of other stereoisomers, more preferably less than 5% of other stereoisomers and most preferably less than 2% of other stereoisomers, are present. Methods of obtaining or synthesizing diastereomers are well known in the art and may be applied as practicable to final compounds or to starting material or intermediates. Other embodiments are those wherein the compound is an isolated compound.

The compounds of the invention may be synthesized by well-known techniques. The starting materials and certain intermediates used in the synthesis of the compounds of this invention are available from commercial sources or may themselves be synthesized using reagents and techniques known in the art, including those synthesis schemes delineated herein. See, for instance, Christensen J A and Squires R F, U.S. Pat. No. 4,007,196, to Ferrosan; Ward N, U.S. Pat. No. 6,172,233, to SmithKline Beecham; Liu L T et. al., U.S. Pat. No. 6,833,458 to Development Center for Biotechnology; Jacewicz V W et. al., U.S. Pat. No. 6,716,985 to SmithKline Beecham; Hoorn H J et. al., U.S. Pat. No. 6,703,408 to Synthon BCT Technologies; Rossi R et. al., U.S. Pat. No. 6,583,287 to Recordati; Brennan J P, U.S. Pat. No. 6,326,496 to Knoll; Murthy K S K and Rey A W, U.S. Pat. No. 5,962,689 to Brantford Chemicals; Adger B M et. al., U.S. Pat. No. 6,066,737 to Chirotech; Lawrie K W M et. al., J. Label. Compd. Radiopharm. 1993 33: 777; Willcocks K et. al., J. Label. Compd. Radiopharm. 1993 33: 777; Zepp C M, U.S. Pat. No. 5,258,517 to Sepracor; Czibula, L et. al., Eur. J. Org. Chem. 2004 15: 3336; Hughes G et. al., J. Am. Chem. Soc. 2003 125: 11253; Johnson T A et. al., J. Am. Chem. Soc. 2001 123: 1004; and US Patent Applications 20030004352, 20030220370, 20040073038, 20040073038, 20030018048, and 20040215020; each of which documents is incorporated herein by reference.

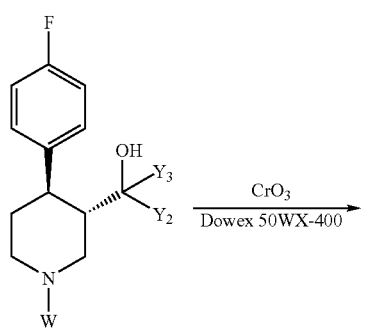

Formula VI
W = CH₃
Y₂ = Y₃ = H

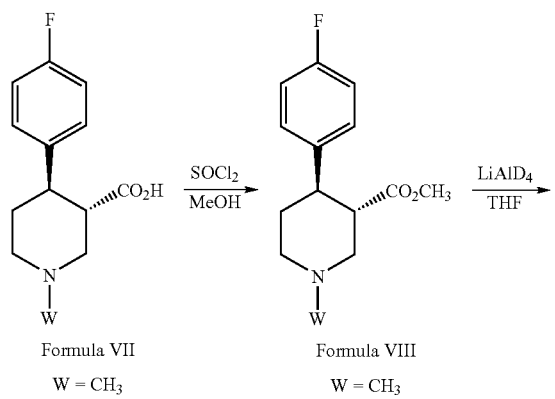

Formula VII
W = CH₃

Formula VIII
W = CH₃

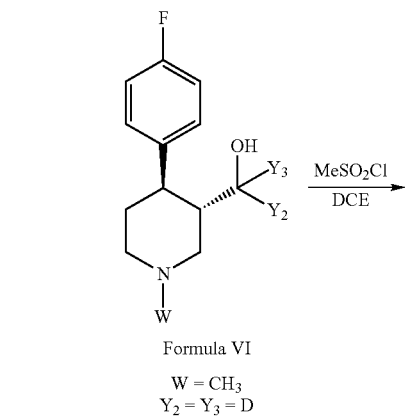

Formula VI
W = CH₃
Y₂ = Y₃ = D

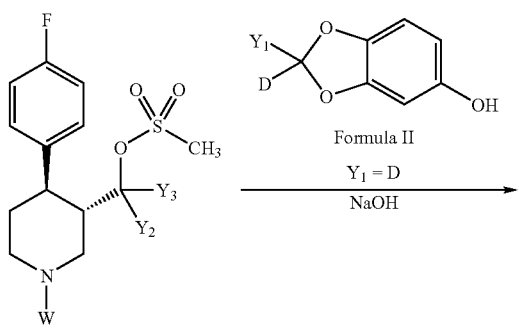

Formula IX
W = CH₃
Y₂ = Y₃ = D

Formula II
Y₁ = D

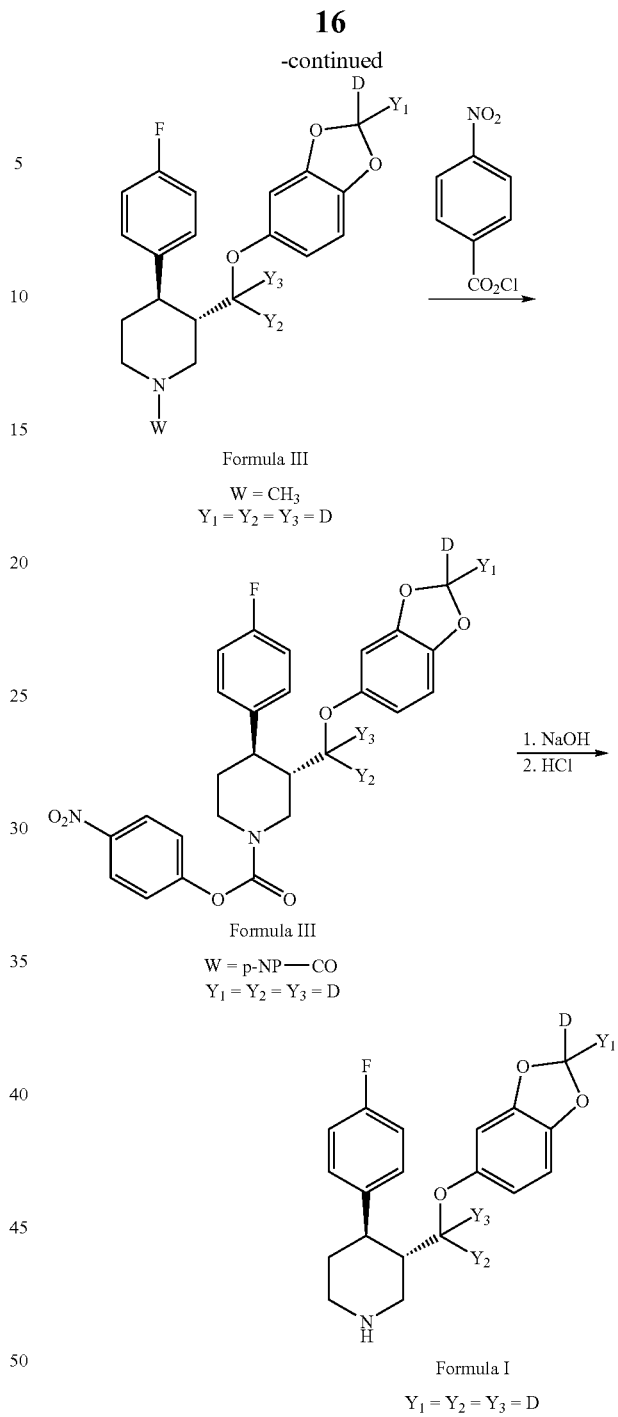

Formula III
W = CH₃
Y₁ = Y₂ = Y₃ = D

Formula III
W = p-NP—CO
Y₁ = Y₂ = Y₃ = D

Formula I
Y₁ = Y₂ = Y₃ = D

A convenient method for producing a compound of formula I is shown graphically in scheme II, wherein D represents deuterium, each Y is independently selected from hydrogen or deuterium, and W is a nitrogen protecting group. Nitrogen protecting groups are well known in the art and include, but are not limited to methyl, ethyl benzyl, substituted benzyl, allyl; and $C_{1-6}$ alkylene carbamates such as phenyl carbamate, substituted phenyl carbamate, benzyl carbamate, substituted benzyl carbamate, vinyl carbamate, or allyl carbamate. Preferred nitrogen protecting groups are methyl, ethyl benzyl, 4-substituted benzyl, tert-butyl carbamate, benzyl carbamate, methyl carbamate, ethyl carbamate, propyl carbamate, vinyl carbamate, and allyl carbamate are preferred. More preferred W groups include methyl, ethyl benzyl, methyl carbamate, ethyl carbamate, vinyl carbamate, allyl carbamate, phenyl carbamate, benzyl carbamate, and tert-butyl carbamate. Suitable benzyl substituents include, for instance, $C_{1-4}$ alkyl, $C_{1-4}$ alkyl-O—, fluoro, chloro, and nitro. Each of compounds of formula I-III and VI-IX may optionally be further substituted with deuterium in place of hydrogen and $^{13}C$ in place of $^{12}C$. In each of formulae I-III, $Y^1$ is preferably deuterium.

Reaction of compounds of formula VI with compounds of formula II may be carried out in a single step, for instance by the Mitsunobu reaction (see e.g. Mitsunobu O, Synthesis 1981, 1) using a suitable phosphine such as triphenylphosphine or tributylphosphine, among others, and an azodicarboxylates such as, for instance, diethylazodicarboxylate, diisopropylazodicarboxylate, or dibenzylazodicarboxylate. Alternatively, as shown in scheme II, the alcohol may be converted to a displaceable electrophile, for instance by producing a sulfate or sulfonate ester (e.g., such as a compound of formula IX) or by replacing the oxygen with a halogen such as chloride, bromide, or iodide. Suitable sulfate or sulfonate esters include, but are not limited to, tosylate, mesylate, brosylate, nosylate, and triflate. One route to compounds of formula III is reaction of compounds of formula VI, wherein W is methyl, with thionyl chloride to give the primary chloride, and displacement with the compound of formula II under basic conditions using an alkali metal base such as sodium or potassium, e.g. in the form of sodium methoxide or sodium ethoxide. Another route, as shown in Scheme II, is reaction of compounds of formula VI, wherein W is methyl, with a sulfonyl chloride (such as methanesulfonyl chloride) to give the sulfonate, and displacement with the compound of formula II under basic conditions using a base such as sodium hydroxide (see, e.g., Examples 28 and 29, infra).

Compounds of formula III wherein W is methyl or ethyl may be N-deprotected by a 2-step sequence involving first a chloroformate (e.g. phenyl chloroformate, methyl chloroformate, ethyl chloroformate, or vinyl chloroformate, among others) to simultaneously N-dealkylate the piperidine ring and form the carbamate corresponding to the chloroformate used. In the case of simple alkyl or aryl chloroformates, the resulting carbamate is then hydrolyzed with strong base, such as aqueous KOH, to yield the compound of formula I. Vinyl carbamates, produced upon reacting compounds of formula III with vinyl chloroformate, may be decomposed with acid, such as HCl, to yield the product of formula I. If W is benzyl or substituted benzyl, the compound of formula III may be N-deprotected by hydrogenation, for instance using a palladium catalyst such as palladium metal or $Pd(OH)_2$ on carbon together with either hydrogen gas or an alternate hydrogen donor, such as formic acid or ammonium formate. If W is benzyl carbamate it may be deprotected in a manner similar to a benzyl group, or removed by acidolysis, for instance using hydrogen bromide. If W is tert-butyl carbamate, the compound of formula III may be N-deprotected by treatment with acid (for example, hydrogen chloride, hydrogen bromide, trifluoroacetic acid, or p-toluenesulfonic acid). The use and removal of nitrogen protecting groups is well known in the art, and many additional methods for protecting and deprotecting the piperidine ring nitrogen will be evident to those of ordinary skill in organic synthesis.

Compounds of formula II can be readily synthesized by hydrolysis of esters formed by oxidation of the 5-formyl- or 5-keto-1,3-benzodioxols, respectively; by metal-halogen exchange from a 5-halo-1,3-benzodioxol and quenching with water; or by oxidative decarboxylation of 5-benzodioxol acids. See e.g. Borzatta V et. al., PCT International Application WO 2004092106; Kuo L-H et. al., US Patent Application 2002123655, Sinon Corporation Applicant; Pansegrau P D and Munson B P, U.S. Pat. No. 5,840,997 to Dakota Gasification; and Zambrano J L and Dorta R, Synlett 2003 10: 1545. The precursor deuterated benzodioxols of formula V are readily available by means known in the art of organic synthesis. For instance, reaction of a deuterated methylenation reagent with an appropriate catechol of formula IV, such as 3,4-dihydroxybromobenzene, 3,4-dihydroxybenzaldehyde, 1-(3,4-dihydroxyphenyl)-oxo-alkanes, or 1-(3,4-dihydroxyphenyl)-oxo-arenes, will result in ring closure to the corresponding benzodioxol. Examples of suitable deuterated methylenation reagents include, for instance, mono and dideuterated forms of dihalomethanes such as dichloromethane, dibromomethane, bromochloromethane, or diiodomethane. The synthesis of benzodioxols from catechol (o-dihydroxyphenyl) precursors is well known in the art and is described for instance by Cabedo N et. al., J. Med. Chem. 2001 44: 1794; Walz A J and Sundberg R J, J. Org. Chem. 2000 65: 8001; Orús L et. al., J. Med. Chem. 2002 45: 4128; Chang J et. al., Helv. Chim. Acta 2003 86: 2239; Moreau A et. al., Tetrahedron 2004 60: 6169; and Panseri P et. al., U.S. Pat. No. 5,936,103 to Borregaard Italia. Each of the above-named publications is herein incorporated by reference.

U.S. Pat. No. 5,936,103 provides an efficient method that can be adapted to the readily available dichlorodideuteromethane to produce preferred compounds of formulae I and III wherein Y is deuterium as set forth in scheme III, below.

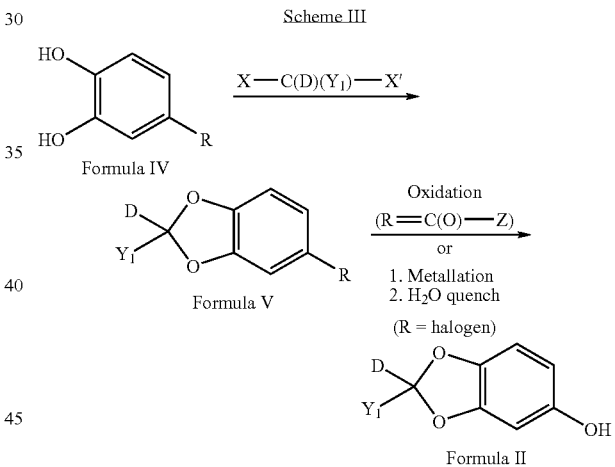

Scheme III

In Scheme III, R represents a halide such as bromo, chloro, or iodo; or an oxo group such as formyl, methyl ketone, ethyl ketone, or phenyl ketone; D is deuterium; Y is hydrogen or deuterium; X and X' are independently halide such as bromo, chloro, or iodo; and Z is hydrogen, lower alkyl such as $C_{1-4}$ alkyl, or aryl such as phenyl or substituted phenyl.

Further deuterium substitution can be accomplished in compounds of formula II. For instance, halogenation ortho to the hydroxyl group, e.g. using N-bromosuccinimide in an ionic liquid, followed by O-protection (for instance with a silyl group such as triethylsilyl or tert-butyldimethylsilyl, among others), halogen-metal exchange and deuterium quench such as with $D_2O$, or alternatively catalytic hydrogenation under deuterium gas, produces the 6-deuterobenzodioxol derivative (see e.g. Yadav J S et. al., Adv. Synth. Catal. 2004 346: 77; Kirefu T, et. al. J. Label. Compd. Radiopharm. 2001 44: 329). Starting from 1,4-dibromo-2,3-dimethoxybenzene, halogen-deuterium exchange by similar means provides 1,2-dimethoxy-3,6-dideuterobenzene (e.g. see Albrecht M, Synthesis 1996: 230). Cleavage of the methoxy groups, for instance with boron tribromide, followed by deuteromethyleneation as described above, yields 2-deuterium substituted 4,7-dideutero-1,3-benzodioxol, which can be converted to 4,7-dideutero derivatives of formula II by known means (see e.g. DePriest R N, U.S. Pat. No. 4,940,807 to Ethyl Corporation; Feugeas C, Bull. Chim. Soc. Fr. 1964: 1982). Other methods of aromatic substitution suitable for incorporation of deuterium are known to those of skill in the art of organic synthesis.

Isotopic substitution elsewhere in compounds of formula II can also be accomplished by means known in the art. For instance, 1,3-propanediol is commercially available in numerous isotopic forms, e.g. 1,3-propanediol-$^{13}C_3$ (Sigma Aldrich (ISOTEC), St. Louis, Mo.); 1,3-propanediol-2-$^{13}C$ (Sigma Aldrich (ISOTEC), St. Louis, Mo.); 1,3-propanediol-$d_8$ (C/D/N Isotopes, Pointe-Claire, Quebec, Canada); and 1,3-propane-2,2-$d_2$-diol (C/D/N Isotopes, Pointe-Claire, Quebec, Canada). This starting material is readily converted to the known compound 4 as shown below in scheme IV. For example, monodeprotonation of the diol and mono-protection (e.g. with a tert-butyldimethylsilyl group), followed by oxidation of the free alcohol to an aldehyde (e.g. Swern oxidation), and reaction with a 4-metallated-fluorobenzene (e.g. 4-bromofluorobenene deprotonated with n-butyl-lithium) produces intermediate compound 3.

Deprotection of the secondary alcohol (e.g. as a tetrahydropyran ether, by reaction with dihydropyran), O-deprotection of the primary alcohol (e.g. a fluoride source such as KF in dimethylformamide if silyl protection is used), activation of the resulting primary alcohol (e.g. as a chloride using triphenylphosphine/carbon tetrachloride) and reaction with p-anisidine, followed by oxidation of the protected secondary alcohol to a ketone (e.g. direct oxidation of the THP ether using an acidic oxidizing agent, or hydrolytic removal of the THP ether followed by oxidation), can be carried out to produce compound 4. Transformation of Compound 4 to Compound 7 (equivalent to formula VI wherein W is tert-butoxycarbonyl) is described by Hughes G et. al., J. Am. Chem. Soc. 2003 125: 11253. Reaction of compound 7 with compounds of formula II and subsequent N-deprotection to yield compounds of formula I can be accomplished analogously to the sequence shown in scheme II although, as will be recognized, without the need for transformation of the N-methyl group to a carbamate as shown in scheme II.

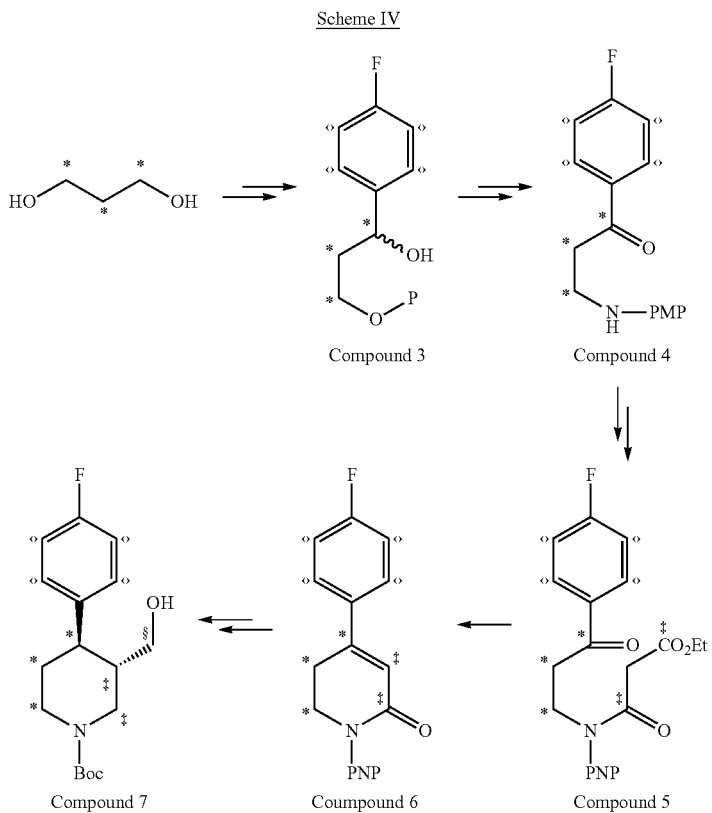

Scheme IV

In Scheme IV, P represents a suitable oxygen protecting group known in the art of organic synthesis. Useful oxygen protecting groups include, but are not limited to, $C_{1-4}$ alkylene, benzyl, $C_{1-2}$-oxymethyl, or tri-$C_{1-6}$-silyl. PMP represent 4-methoxyphenyl. Boc represents tert-butyoxycarbonyl. Different molecular positions are labeled to indicate sources of potential isotopic substitution: "*" shows $^{13}C$ substitution arising from labeled 1,3-propanediol. The piperidine 5 and 6 positions can be deuterium labeled from 1,3-propanediol as well. "< >" shows deuterium substitution from labeled 4-bromo-fluorobenzene (e.g. C/D/N isotopes). "‡" indicates $^{13}C$ labels arising from the labeled diethyl malonate (e.g. Aldrich); "§" indicates $^{13}C$ or deuterium labels arising, respectively, from carrying out installation of the hydroxymethyl group using a $^{13}C$-labeled acylating group such as dimethyl carbonate-$^{13}C$ (readily produced from $^{13}C$-phosgene (e.g. Isotec) and methanol), or by reduction of the resulting ester group with a suitable deuterated "hydride" donor such as deuteroborane (see e.g. Kinugawa Y and Kawashima E, Nucleic Acids Res. Suppl. 2002: 19; Turecek F and Hanus V, Org. Mass Spec. 1980 15: 8).

It will be recognized that any single step or combination of labeling steps shown in scheme IV are feasible. The synthetic sequence and reagents in scheme IV illustrate the potential for broad incorporation of stable isotopic labels throughout compounds of formula I by known means, but are not intended to limit the scope of the invention. Other means of introducing isotopic labels into compounds of formula I will be apparent to those of skill in organic chemistry, and different approaches to compounds of formula I will enable or simplify labeling of different atoms. Thus, substitution of carbons and hydrogens in compounds of this invention by $^{13}C$ and deuterium, respectively, is within the means of the ordinarily skilled practitioner of organic synthesis.

The specific approaches and compounds shown above are not intended to be limiting. Additional methods of synthesizing compounds of formula I and their synthetic precursors, including those within routes not explicitly shown in Schemes herein, are within the means of chemists of ordinary skill in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier M D L), or interne search engines such as Google® or keyword databases such as the US Patent and Trademark Office text database.

Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jahnisch, K et al, Angew. Chem. Int. Ed. Engl. 2004 43: 406; and references therein).

The synthetic methods described herein may also additionally include steps, either before or after any of the steps described in Schemes II or III, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, chromatography).

According to another embodiment, the invention provides an intermediate compound of formula II or formula III, wherein each hydrogen and carbon atom is optionally substituted by deuterium and $^{13}C$, respectively.

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to enhanced serotonin neurotransmission).

The term "isotopologue" refers to species that differ from a specific compound of this invention only in the isotopic composition of their molecules or ions. The terms "lighter isotopologue" and "lighter atom isotopologue" as used herein, refer to species that differs from a compound of this invention in that it comprises one or more light isotopic atoms $^{1}H$ or $^{12}C$ at positions occupied by a deuterium or $^{13}C$ in the specific compound of this invention. For the purposes of this invention, $^{11}C$ is not referred to as a light isotope of carbon.

A specific compound of this invention may also be referred to as a "heavy atom isotopic compound" to distinguish it from its lighter isotopologues when discussing mixtures of isotopologues. This is because a specific compound and all of its lighter isotopologues, except for Compound 1, are compounds of Formula I.

Chemical naming terminology can be complex and different chemical names can often reasonably be applied to the same structure. To avoid any confusion, "Compound 1" refers to the free base form of the active serotonin reuptake inhibiting agent of the drug approved by the US FDA in NDA nos. 020710, and 020936.

It will be recognized that many commonly occurring atoms in biological systems exist naturally as mixtures of isotopes. Thus, Compound 1 inherently comprises small amounts of deuterated and/or $^{13}C$-containing isotopologues. The present invention distinguishes such forms having minor amounts of such isotopologues from its scope in that the term "compound" as used in this invention refers to a composition of matter that is predominantly a specific isotopologue. A compound, as defined herein, in embodiments contains less than 10%, preferably less than 6%, and more preferably less than 3% of all other isotopologues, including the Compound 1. Compositions of matter that may contain greater than 10% of all other specific isotopologues combined are referred to herein as mixtures and must meet the parameters set forth below. These limits of isotopic composition, and all references to isotopic composition herein, refer solely to the active, free base form of the compound of Formula I, and do not include the isotopic composition of hydrolysable portions of prodrugs, or of counterions, certain of which, such as chloride and bromide, exist naturally as mixtures comprising substantial percentages of multiple isotopes.

The term "heavy atom" refers to isotopes of higher atomic weight than the predominant naturally occurring isotope.

The term "stable heavy atom" refers to non-radioactive heavy atoms.

Both "$^{2}H$" and "D" refer to deuterium.

"Stereoisomer" refers to both enantiomers and diastereomers

"Nos." refers to numbers

"PDE" refers to cyclic guanosine monophosphate-specific phosphodiesterase

"cGMP" refers to cyclic guanosine monophosphate

"5'-GMP" refers to guanosine-5'-monophosphate

"cAMP" refers to cyclic adenosine monophosphate

"5'-AMP" refers to adenosine-5'-monophosphate

"PM" refers to poor metabolizer

"EM" refers to extensive metabolizer

"AIBN" refers to 2,2'-azo-bis(isobutyronitrile)

"Boc" refers to tert-butoxycarbonyl

"PMP" refers to 4-methoxyphenyl

"DHP" refers to dihydropyran

"THP" refers to tetrahydropyran

"THF" refers to tetrahydrofuran

"DMF" refers to N,N-dimethylformamide
"DMSO" refers to dimethylsulfoxide
"alkylene" refers to a straight, branched, or partially or wholly cyclic alkyl group which may contain one or more degrees of unsaturation in the form of cis, trans, or mixed cis, trans-double bonds, or triple bonds "aq." Refers to aqueous
"h" refers to hours
"min" refers to minutes
"tert" refers to tertiary
"brine" refers to saturated aqueous sodium chloride
"US" refers to the United States of America
"FDA" refers to Food and Drug Administration
"NDA" refers to New Drug Application
"AUC" refers to area under the plasma-time concentration curve
CYP3A4 refers to cytochrome P450 oxidase isoform 3A4
"MC-4R" refers to the human melanocortin-4 receptor
"5-HT" refers to 5-hydroxytryptamine or serotonin
"NEP" refers to neutral endopeptidase (EC 3.4.24.11)
"HMG-CoA" refers to 3-hydroxy-3-methylglutaryl-coenzyme A
"ETA" refers to endothelin subtype A receptors
"ETB" refers to endothelin subtype B receptors
"SSRI" refers to selective serotonin reuptake inhibitor
"PPAR" refers to peroxisome proliferator-activated receptor
"Ed." refers to editor The invention further provides compositions comprising a mixture of a compound of this invention and its lighter isotopologues. These mixtures may occur, for instance, simply as the result of an inefficiency of incorporating an isotope at a given position; intentional or inadvertent exchange of protons for deuterium, e.g. exchange of bulk solvent for heteroatom-attached deuterium; or intentional mixtures of pure compounds.

In one embodiment, such mixtures comprise at least about 50% of the heavy atom isotopic compound (i.e., less than about 50% of lighter isotopologues). More preferable is a mixture comprising at least 80% of the heavy atom isotopic compound. Most preferable is a mixture comprising 90% of the heavy atom isotopic compound.

In an alternate embodiment the mixture comprises a compound of Formula I and its lighter isotopologues in relative proportions such that at least about 50%, preferably at least 80%, more preferably at least 90%, even more preferably at least 95% and most preferably at least 98% of the compounds in said mixture comprise a heavy atom isotope at each position containing a stable heavy atom isotope in the heavy atom isotopic compound. The following exemplifies this definition. A hypothetical compound of the invention contains deuterium at positions $Y^1$, $Y^2$ and $Y^3$. A mixture comprising this compound and all of its potential lighter isotopologues and the relative proportion of each is set forth in the table below.

TABLE 1

|  | $Y^1$ | $Y^2$ | $Y^3$ | Relative Amt |
|---|---|---|---|---|
| Compound | D | D | D | 40% |
| Isotopologue 1 | D | D | H | 15% |
| Isotopologue 2 | D | H | D | 14% |
| Isotopologue 3 | H | D | D | 13% |
| Isotopologue 4 | D | H | H | 6% |
| Isotopologue 5 | H | D | H | 5% |
| Isotopologue 6 | H | H | D | 4% |
| Isotopologue 7 | H | H | H | 3% |
| % of compounds comprising an isotope at position indicated position | (40% + 15% + 14% + 6%) = 75% | (40% + 15% + 13% + 5%) = 73% | (40% + 14% + 13% + 4%) = 72% |  |

From the table it can be seen that the compound plus lighter isotopologues 1, 2 and 4 comprise the isotope deuterium at position $Y^1$. These compounds are present in the mixture at relevant amounts of 40%, 15%, 14% and 6%. Thus, 75% of the mixture comprises the isotope at $Y^1$ that is present in the compound. The compound plus lighter isotopologues 1, 3 and 5 comprise the isotope deuterium at position $Y^2$. These compounds are present in the mixture at relevant amounts of 40%, 15%, 13% and 5%. Thus, 73% of the mixture comprises the isotope at $Y^2$ that is present in the compound. The compound plus lighter isotopologues 2, 3 and 6 comprise the isotope deuterium at position $Y^3$. These compounds are present in the mixture at relevant amounts of 40%, 14%, 13% and 4%. Thus, 71% of the mixture comprises the isotope at $Y^3$ that is present in the compound. Accordingly, this mixture comprises a compound and its lighter isotopologues in relative proportions such that 71% of the compounds in said mixture comprise an isotope at each position containing a stable heavy atom isotope in the full isotopic compound.

The invention also provides compositions comprising an effective amount of a compound of any one of formulae I, II or III or a salt thereof; or a prodrug or a salt of a prodrug thereof; or a solvate, hydrate, or polymorph thereof, if applicable; an acceptable carrier. The carrier(s) must be "acceptable" in the sense of being compatible with the other ingredients of the formulation.

In a preferred embodiment, the invention provides a composition comprising a compound of formula I, or a pharmaceutically acceptable salt, prodrug or pharmaceutically acceptable prodrug salt thereof; or a solvate, hydrate or polymorph of any of the foregoing and a pharmaceutically acceptable carrier, wherein said composition is formulated for pharmaceutical use ("a pharmaceutical composition"). A "pharmaceutically acceptable carrier" is a carrier that is compatible with the other ingredients of the composition and not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US Patents, some of which include, but are not limited to, U.S. Pat. Nos. 4,369,172; and 4,842,866; 5,807,574; and references cited therein. Coatings can be used for delivery of compounds to the intestine (see, e.g., U.S. Pat. Nos. 6,548,084, 6,638,534, 5,217,720, and 6,569,457, 6,461,631, 6,528,080, 6,800,663, and references cited therein), or they may be non-eroding and designed to allow release of an active agent by extrusion (see, e.g. U.S. Pat. No. 6,706,283). Each of these patents is incorporated herein by reference.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. Surfactants such as sodium lauryl sulfate may be useful to enhance dissolution and absorption.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be administered in the form of suppositories for rectal or vaginal administration. These compositions can be prepared by mixing a compound of Formula I with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Such administration is known to be effective with erectile dysfunction drugs: Rabinowitz J D and Zaffaroni A C, U.S. Pat. No. 6,803,031, assigned to Alexza Molecular Delivery Corporation.

Application of the subject therapeutics may be local, so as to be administered at the site of interest. Various techniques can be used for providing the subject pharmaceutical compositions at the site of interest, such as injection, use of catheters, trocars, projectiles, pluronic gel, stents, sustained drug release polymers or other device which provides for internal access.

Thus, according to another embodiment, a compound of Formula I may be incorporated into a pharmaceutical composition for coating an implantable medical device, such as prostheses, artificial valves, vascular grafts, stents, or catheters. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings are optionally further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating or filling an implantable drug release device comprising the step of contacting said drug release device with a compound of formula I or a pharmaceutical composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound of Formula I or a pharmaceutical composition of this invention, such that said compound is therapeutically active.

According to another embodiment, the invention provides an implantable drug release device impregnated with or containing a compound of Formula I or a pharmaceutical composition of this invention, such that said compound is released form said device and is therapeutically active.

Where an organ or tissue is accessible because of removal from the patient, such organ or tissue may be bathed in a medium containing a pharmaceutical composition of this invention, a pharmaceutical composition of this invention may be painted onto the organ, or a pharmaceutical composition of this invention may be applied in any other convenient way.

The present invention further provides pharmaceutical compositions comprising an effective amount of one or more compound of Formula I, in combination with an effective amount of one or more second therapeutic agents useful for treating or preventing a condition selected from depression, hypertension, generalized anxiety disorder, phobias, post-traumatic stress syndrome, avoidant personality disorder, sexual dysfunction; eating disorders including bulimia, anorexia nervosa, and binge eating; obesity, chemical dependencies, cluster headache, migraine; pain, including neuropathic pain, diabetic nephropathy, post-operative pain, psychogenic pain disorders, and chronic pain syndrome; Alzheimer's disease, obsessive-compulsive disorder, panic disorder with or without agoraphobia, memory disorders, Parkinson's diseases, endocrine disorders, vasospasm, cerebellar ataxia, gastrointestinal tract disorders, negative symptoms of schizophrenia, premenstrual syndrome, Fibromyalgia Syndrome; urinary incontinence, including stress incontinence; Tourette's syndrome, trichotillomania, kleptomania, male impotence, cancer, chronic paroxysmal hemicrania and headache in a mammal, sleep-related breathing disorders, cognitive deficits due to aging, stroke, head trauma, neurodegenerative diseases, schizophrenia, anxiety, aggression and stress, disorders of thermoregulation, respiratory disease, bipolar disorder, psychosis, sleep disorder, mania, acute mania, bladder disorder, genitourinary disorder, cough, emesis, nausea, and psychotic disorders such as paranoia and manic-depressive illness, tic disorder, diabetic cardiomyopathy, diabetic retinopathy, cataracts, myocardial infarction, prolonged fatigue, chronic fatigue, chronic fatigue syndrome, premature ejaculation, dysphoria, post partum depression, social phobia, disruptive behavior disorders, impulse control disorders, borderline personality disorder, attention deficit disorders without hyperactivity, Shy-Drager Syndrome, cerebral ischemia, spinal cord trauma, Huntington's Chorea, amyotrophic lateral sclerosis, AIDS-induced dementia, muscular spasms, convulsions, perinatal hypoxia, hypoxia, cardiac arrest, hypoglycemic neuronal damage, ocular damage and retinopathy, brain edema, tardive dyskinesia and cerebral deficits subsequent to cardiac bypass surgery and grafting, affective disorders, mood disorders agoraphobia without history of panic disorder, an acute stress disorder, autism, dyskinesia, disthymic disorder; obesity due to genetic or environmental causes, polycycstic ovary disease, craniopharyngeoma, Prader-Willi Syndrome, Frohlich's Syndrome, Type II diabetes, growth hormone deficiency, and Turner's Syndrome; excessive or undesired proinflammatory cytokine secretion or production, jet lag, insomnia, hypersomnia, nocturnal enuresis, restless-legs syndrome, vaso-occlusive events, hyperglycemia, hyperinsulinaemia, hyperlipidaemia, hypertriglyceridemia, diabetes, insulin resistance, impaired glucose metabolism, conditions of impaired glucose tolerance (IGT), conditions of impaired fasting plasma glucose, glomerulosclerosis, syndrome X, coronary heart disease, angina pectoris, vascular restenosis, endothelial dysfunction, impaired vascular compliance, or congestive heart failure; and a pharmaceutically acceptable carrier.

Also within the scope of this invention are pharmaceutical compositions comprising an effective amount of a compound of Formula I, or a pharmaceutically acceptable salt thereof; or a prodrug or a pharmaceutically acceptable salt of a prodrug thereof; or a solvate, hydrate, or polymorph thereof; in combination with an effective amount of a second therapeutic agent useful for reducing the side effects of Compound 1, for enhancing or potentiating the activity of Compound 1, or for increasing the duration of pharmacological action of Compound 1; and a pharmaceutically acceptable carrier.

Additional therapeutic agents useful in combination with the compounds of this invention include, but are not limited to: 5-$HT_{1A}$ antagonist or ligand; an $NK_1$-receptor antagonist; a serotonin receptor antagonist; 2-amino-4,5,6,7-tetrahydro-6-propylamino-benzothiazole (pramipexole), the (+)- or (−)-enantiomer thereof; a sulfamate anticonvulsant agent; a precursor or prodrug of serotonin, or an intermediate in the biosynthesis of serotonin; selective agonists and antagonists of one or both of the 5-$HT_{1A}$ and 5-$HT_{1D}$ receptors; a composition containing dimethylaminoethanol (DMAE), omega 3-fatty acids, betaine, oligomeric proanthocyanidins, folic acid, vitamins C, E, $B_{12}$, $B_6$, $B_5$ and beta-carotene and minerals (calcium, magnesium, zinc and selenium); naltrexone; cyclobenzaprine, or metabolites thereof; olanzapine; olanazapine-N-oxide; 2-hydroxymethylolanzapine; an atypical antipsychotic; tramadol; an aldose reductase inhibitor, or a prodrug thereof; 1-threo-methylphenidate; a Type III, Type IV, mixed Type III-Type IV, or Type V phosphodiesterase inhibitor, or an ester, amide, prodrug, active metabolite, or combination thereof; a substituted indole estrogenic agent; (+)-1-(3,4-dichlorophenyl)-3-azabicyclo[3.1.0]hexane; folic acid; methyltetrahydrofolate; WAY 100635; betaxolol; (R)-3-N,N-dicyclobutylamino-8-fluoro-3,4-dihydro-2H-1-benzopyran-5-carboxamide hydrogen (2R,3R)-tartrate monohydrate; R-tofisopam; N-acetyl-serotonin; a DRD2-specific dopamine agonist; a $5HT_4$ receptor antagonist; nalmefene; moxonidine; mirtazapine; chromium; a cyclooxygenase-2 selective inhibitor; a $5HT_{2A}$ selective receptor antagonist; a $CB_1$ receptor antagonist; a MCH-1R receptor antagonist; a tetra-substituted pyrimidopyrimidine; a selective dopamine $D_4$ receptor ligand; trimebutine, fedotozine and mixtures thereof; an NMDA partial receptor agonist; an NMDA receptor antagonist; a cholinesterase inhibitor; a GSK-3 inhibitor; an alpha-2-delta ligand or a prodrug thereof; an extract of kava; a norepinephrine reuptake inhibitor; a corticosteroid; a non-steroidal immunophilin-dependent immunosuppressant; N-desmethylclozapine; an (R)-2,3-benzodiazepine as disclosed in US Patent Application 20040224943; a selective neuronal nitric oxide synthase inhibitor; modafinil; a selective oxytocin antagonist; a nicotine receptor antagonist; an adenosine A2a receptor antagonist; a 5-$HT_{2c}$ receptor antagonist; an AMPA receptor potentiator; a nicotine partial agonist; irindalone; a delta opioid receptor ligand; a growth hormone secretagogue; p-chloro-N-(2-morpholinoethyl)-benzamide and its metabolites; a pharmaceutically acceptable salt of any of the said additional therapeutic agents; or combinations of two or more of the foregoing.

Examples of 5-$HT_{1A}$ antagonists and ligands include, but are not limited to, alprenolol, WAY 100135, WAY 100635, spiperone, pindolol, (S)-UH-301, penbutolol, propranolol, tertatolol; (R)-5-carbamoyl-8-fluoro-3-N,N-disubstituted-amino-3,4-dihydro-2H-1-benzopyran; and those disclosed in U.S. Pat. Nos. 5,776,969; 5,958,429; 6,136,861; 6,656,951; 6,780,860; 6,815,448; 6,821,981; 6,861,427; 6,894,053; and US Patent Application 20050085475.

Examples of $NK_1$-receptor antagonists include, but are not limited to, those disclosed in U.S. Pat. Nos. 6,162,805; 6,878,732; US Patent Application 20050137208; as well as CNS-penetrant agents capable of inhibiting NK-1 receptor agonist-induced foot tapping in the gerbil, or attenuating separation-induced vocalizations by guinea-pig pups.

Examples of sulfamate anticonvulsant agents include, but are not limited to, topiramate and those disclosed in and referenced by U.S. Pat. No. 5,384,327.

Examples of precursors or prodrugs of serotonin, and intermediates in the biosynthesis of serotonin, include but are not limited to, L-tryptophan, L-5-hydroxytryptophan, diethyl N-benzyloxycarbonyl-5-benzyloxycarbonyloxy-L-tryptophyl-L-aspartate, dibenzyl N-benzyloxycarbonyl-5-hydroxy-L-tryptophanylaspartate, 5-Hydroxy-L-tryptophyl-L-aspartic acid trihydrate, diethyl N-benzyloxycarbonyl-5-hydroxy-L-tryptophyl-L-glutamate, diethyl 5-hydroxy-L-tryptophyl-L-glutamate hydrochloride, dibenzyl L-benzyloxycarbonyl-5-hydroxytryptophyl-L-glutamate, 5-hydroxy-L-tryptophyl-L-glutamic acid, pentachlorophenyl ester of N-benzyloxycarbonyl-5-hydroxy-L-tryptophan, methyl ester of N-benzyloxycarbonyl-5-hydroxy-L-tryptophyl-L-tyrosine, N-Acetyl-5-hydroxy-L-tryptophan, methyl ester of N-acetyl-5-hydroxy-L-tryptophyl-L-tyrosine, methyl ester of n-acetyl-5-hydroxy-L-tryptophyl-5-hydroxy-L-tryptophan, 5-hydroxy-L-tryptophyl-L-alanine hydrate, 5-hydroxy-L-tryptophan-L-valine, 5-hydroxy-L-tryptophyl-L-leucine, 5-hydroxy-L-tryptophyl-L-proline, 5-hydroxy-L-tryptophyl-L-phenylalanine, 5-hydroxy-L-tryptophyl-5-hydroxy-L-tryptophan, 5-hydroxy-L-tryptophyl-L-tryptophan, 1-5-hydroxytryptophyl-L-serine, 5-hydroxy-L-tryptophyl-L-arginine, 5-hydroxy-L-tryptophylglycine, 5-hydroxyltryptophyl-gamma-aminobutyric acid, 5-hydroxy-L-tryptophanamide hydrate, methyl ester of 5-hydroxy-L-tryptophyl-L-histidine, benzyl ester of L-5-hydroxytryptophan, benzyl ester of N-benzyloxycarbonyl-5-hydroxy-L-tryptophyl-5-hydroxy-L-tryptophan, 5-Hydroxy-L-tryptophyl-5-hydroxy-L-tryptophan hemihydrate, 5-hydroxytryptophan inosinate, theophylline salt of (DL) 5-hydroxytryptophan, and combinations thereof.

Examples of an atypical antipsychotic agents include, but are not limited to, risperidone, clozapine, seroquel, sertindole, ziprasidone, zotepine, olanzapine, iloperidone, Org 5222, melperone, amperozide, SM-9018, JL-13, and pharmaceutically acceptable salts thereof.

Examples of aldose reductase inhibitors include, but are not limited to, fidarestat, epalrestat, minalrestat, SPR-210, and zenarestat or zopolrestat, or a prodrug thereof.

Examples of selective agonists and antagonists of one or both of the 5-$HT_{1A}$ and 5-$HT_{1D}$ receptors include, but are not limited to, those disclosed in U.S. Pat. No. 6,562,813.

Examples of Type III phosphodiesterase inhibitors include, but are not limited to, bipyridines such as aminone, milrinone and olprinone; anagrelide, bemoradan, ibudilast, isomazole, lixazinone, motapizone, olprinone, phthalazinol, pimobendan, quazinone, siguazodan and trequinsin Examples of calcium channel blockers include, but are not limited to, amlodipine, diltiazem, felodipine, isradipine, nicardipine, nifedipine, and verapamil.

Examples of mixed type III-type IV phosphodiesterase inhibitors include, but are not limited to, anagrelide, bemoradan, ibudilast, isomazole, lixazinone, motapizone, olprinone, phthalazinol, pimobendan, quazinone, siguazodan and trequinsin.

Examples of type IV phosphodiesterase inhibitors include, but are not limited to, pyrrolidinones, in particular roliram; quinazolinediones, xanthine derivatives, phenyl ethyl pyridines, tetrahydropyrimidones, diazepine derivatives, oxime carbamates, naphthyridinones, benzofurans, naphthalene derivatives, purine derivatives, imidazolidinones, cyclohexane carboxylic acids, benzamides, pyridopyridazinones, benzothiophenes, etazolate, S-(+)-glaucine, substituted phenyl compounds and substituted biphenyl compounds as further disclosed in U.S. Pat. No. 6,403,597.

Examples of type V phosphodiesterase inhibitors include, but are not limited to, sildenafil, vardenafil, tadalafil, zaprinast, dipyridamole, 3-isobutyl-8-(6-methoxy-isoquinolin-4-ylmethyl)-1-methyl-3,7-dihydro-purine-2,6-dione; and those disclosed in US Patent Applications 20030055070; 20040044005; 20030139429.

Examples of substituted indole estrogenic agents include, but are not limited to, those disclosed in and referenced by U.S. Pat. No. 6,369,051.

An example of a DRD2-specific dopamine agonist includes, but is not limited to, bromocriptine.

Examples of 5HT$_4$ receptor antagonists include, but are not limited to, A-85380, SB 204070, SB 207226, SB 207058, SB 207710, SB 205800, SB 203186, SDZ 205557, N 3389, FK 1052, SC 56184, SC 53606, DAU 6285, GR 125487, GR 113808, RS 23597, RS 39604, LY-353433 and R 50595.

Examples of cyclooxygenase-2 selective inhibitors include, but are not limited to, celecoxib, valdecoxib, deracoxib, rofecoxib, etoricoxib, tilmacoxib, cimicoxib, and those disclosed in and referenced by US Patent Applications 20050080084 and 20050085477.

Examples of 5-HT$_{2a}$ receptor antagonists include, but are not limited to, those disclosed and referenced by US Patent application 20050070577.

Examples of CB$_1$ receptor antagonists include, but are not limited to, rimonabant and those disclosed in and referenced by US Patent applications 20040248956, 20050009870, 20050014786, 20050054659, 20050080087, and 20050143381.

Examples of selective MCH-1R receptor antagonists include, but are not limited to, those disclosed in and referenced by US Patent applications 20050009815 and 20050026915.

Examples of tetra-substituted pyrimidopyrimidines include, but are not limited to, dipyridamole, mopidamole, dipyridamole monoacetate, 2,6-di-(2,2-dimethyl-1,3-dioxolan-4-yl)-methoxy-4,8-di-piperidinopyrimido-pyrimidine; 2,6-bis-(2,3-dimethyoxypropoxy)-4,8-di-piperidinopyrimidopyrimidine; 2,6-bis[N,N-di(2-methoxy)ethyl]-4,6-di-piperidinopyrimidopyrimidine-; and 2,6-bis(diethanolamino)-4,8-di-4-methoxybenzylaminopyrimidopyrimidine-.

Examples of selective dopamine D$_4$ receptor ligands include, but are not limited to, pipamperone, fananserin, L-745,870, PNU-101387G and U-101387.

An example of a NMDA partial receptor agonist includes, but is not limited to, D-cycloserine.

Examples of NMDA receptor antagonists include, but are not limited to, dextromethorphan, dextrorphan, amantadine, and memantine.

Examples of cholinesterase inhibitors include, but are not limited to, tacrine, donepezil, edrophonium, galantamine, physostigmine, eptastigmine, pyridostigmine, neostigmine, ganstigmine, rivastigmine, demecarium, ambenonium, sarin, metrifonate, soman, tabun, and diisopropyl fluorophosphates.

Examples of GSK-3 inhibitors include, but are not limited to, those disclosed and referenced in US Patent Application 20050026946.

Examples of alpha-2-delta ligands include, but are not limited to, gabapentin, pregabalin, [(1R,5R,6S)-6-(aminomethyl)bicyclo[-3.2.0]hept-6-yl]acetic acid, 3-(1-aminomethylcyclohexylmethyl)-4H-[1,2,4]-oxadiazol-5-one, C-[1-(1H-tetrazol-5-ylmethyl)-cycloheptyl]-methylamine, (3S,4S)-(1-aminomethyl-3,4-dimethylcyclopentyl)-acetic acid, (1α,3α,5α)(3-aminomethyl-bicyclo[3.2.0]hept-3-yl)-acetic acid, (3S,5R)-3-aminomethyl-5-methyloctanoic acid, (3S,5R)-3-amino-5-methylheptanoic acid, (3S,5R)-3-amino-5-methylnonanoic acid, and (3S,5R)-3-amino-5-methyloctanoic acid.

Examples of a norephinephrine reuptake inhibitors include, but are not limited to, desipramine, imipramine, amoxapine, nortriptyline, protriptyline, atomoxetine, oxaprotiline, maprotiline, reboxetine, 1-[1-(3-chlorophenyl)-2-(4-methyl-1-piperazinyl)ethyl]cyclohexanol; and those disclosed in US Patent Application 20050014848.

Examples of corticosteroids include, but are not limited to, prednisolone, budesonide, cortisone, dexamethasone, hydrocortisone, methylprednisolone, fluticasone, prednisone, triamcinolone, and diflorasone.

Examples of non-steroidal immunophilin-dependent immunosuppressants include, but are not limited to, cyclosporine, tacrolimus, ISAtx247, ascomycin, pimecrolimus, rapamycin, and everolimus.

Examples of selective neuronal nitric oxide synthase inhibitors include, but are not limited to, those disclosed in US Patent Application 20040229911.

An example of a selective oxytocin antagonist includes, but is not limited to, L-368,899.

Examples of nicotine receptor antagonists include, but are not limited to, mecamylamine, amantadine, pempidine, dihydro-beta-erythroidine, hexamethonium, erysodine, chlorisondamine, trimethaphan camsylate, tubocurarine chloride, d-tubocurarine, and their optical isomers.

Examples of adenosine A2a receptor antagonists include, but are not limited to, those disclosed in US Patent Application 20030139395.

Examples of 5-HT$_{2c}$ receptor antagonists, inverse agonists and partial agonists include, but are not limited to, ketanserin, SB 242084, SB 206553, SB 243213, SB 228356, ritanserin, deramciclane, mirtazepine, mianserine, sertindole, YM 35 992, Ro 60-0795, Org 38457, Org 12962, EGIS 8465 and RS 102221.

Examples of AMPA receptor potentiators include, but are not limited to, [(methylethyl)sulfonyl]{2-[4-(4-{2-[(methylsulfonyl)amino]ethyl}phenyl)phenyl]propyl}amine, {(2R)-2-[4-(4-{2-[(methylsulfonyl)amino]ethyl}phenyl)phenyl]propyl}[(methylethyl)sulfonyl]amine, N-2-(4-(3-thienyl)phenylpropyl-2-propanesulfonamide, [2-fluoro-2-(4-{3-[(methylsulfonyl)amino]phenyl}phenyl)propyl][(methylethyl)sulfonyl]amine, and, separately, each enantiomer of [2-fluoro-2-(4-{3-[(methylsulfonyl)amino]phenyl}phenyl)propyl][(methylethyl)sulfonyl]amine.

Examples of nicotine receptor partial agonists include, but are not limited to, those disclosed in US Patent Applications 20010036943 and 20030109544.

Examples delta opioid receptor ligands include, but are not limited to, those disclosed in and referenced by US Patent Application 20020077323.

Examples of growth hormone secretagogues include, but are not limited to, those disclosed in US Patent Applications 20020002137 and 20020086865.

In another embodiment, the invention provides separate dosage forms of a compound of Formula I and a second therapeutic agent, wherein said compound and said second therapeutic agent are associated with one another. The term "associated with one another" as used herein means that the separate dosage forms are packaged together in the same container (e.g., in separate blister packs attached to one another, in separate compartments of a compartmentalized container, in separate vessels contained in the same box, etc.), or otherwise attached to one another such that it is readily apparent that the separate dosage forms are intended to be sold and administered together (within less than 24 hours of one another, consecutively or simultaneously).

In the pharmaceutical compositions of the invention, a compound of Formula I is present in an effective amount. As used herein, the term "effective amount" refers to an amount which, when administered in a proper dosing regimen, is sufficient to reduce or ameliorate the severity, duration or progression, or enhance function compromised by a disorder associated with insufficient neurotransmission of serotonin, prevent the advancement of a disorder characterized by insufficient neurotransmission of serotonin, cause the regression of a disorder characterized by insufficient neurotransmission of serotonin, or enhance or improve the prophylactic or therapeutic effect(s) of another therapy.

In certain preferred embodiments, treatment according to the invention provides a reduction in or prevention of at least one symptom or manifestation of a disorder that has been linked insufficient neurotransmission of serotonin, as determined in vivo or in vitro inhibition of at least about 10%, more preferably 20%, 30%, 40%, 50%, 60%, 70%, 80%, 90%, 95%, 98% or 99% of cellular serotonin uptake. With respect to inhibition of serotonin reuptake activity, the term "effective amount" means an amount that results in a detectable increase in the amount or concentration serotonin in a patient or in a biological sample, the correction of or relief from a behavior, deficit, symptom, syndrome or disease that has been linked to reduced or insufficient neurotransmission of serotonin, alone or in combination with another agent or agents; or the induction of a behavior, activity or response that has been linked to normalized or increased neurotransmission of serotonin.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of Formula I can range from about 0.001 mg/kg to about 500 mg/kg, more preferably 0.01 mg/kg to about 50 mg/kg, yet more preferably 0.025 mg/kg to about 1.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of that second therapeutic agent is between about 20% and 100% of the dosage normally utilized in a monotherapy regime using just that additional agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents listed above will act synergistically with the compounds of this invention. When this occurs, it will allow the effective dosage of the second therapeutic agent and/or the compound of Formula Ito be reduced from that required in a monotherapy. This has the advantage of minimizing toxic side effects of either the second therapeutic agent or a compound of Formula I, synergistic improvements in efficacy, improved ease of administration or use and/or reduced overall expense of compound preparation or formulation.

Methods of Treatment

In one embodiment, the present invention provides a method of inhibiting the uptake of serotonin in a subject comprising the step of administering to said subject an effective amount of a compound of Formula I, preferably as part of a composition additionally comprising a pharmaceutically acceptable carrier. Preferably this method is employed to treat a subject suffering from or susceptible to one or more disease or disorder selected from depression, obsessive-compulsive disorder, generalized anxiety, post-traumatic stress, major depression, panic disorder, social phobia, premenstrual syndrome, cardiac disorders, non-cardiac chest pain; smoking addiction (to cause cessation or prevent relapses); reducing platelet activation states, alcoholism and alcohol dependence; psychiatric syndromes including anger, rejection sensitivity, and lack of mental of physical energy; late luteal phase dysphoric disorder, premature ejaculation, senile dementia, obesity, Parkinson's disease, or canine affective aggression.

The method can also be employed to treat a subject suffering from or susceptible to inhibition of cancer cell growth, methods for stimulating bone formation by osteoblast stimulation, treatment of dermatological diseases or disorders such as hyperproliferative or inflammatory skin diseases, and treatment of premature female orgasm. Other embodiments include any of the methods herein wherein the subject is identified as in need of the indicated treatment.

More preferably this method is employed to treat a subject suffering from or susceptible to one or more disease or disorder selected from major depressive disorder, obsessive compulsive disorder, panic disorder, social anxiety disorder, generalized anxiety disorder, post-traumatic stress disorder, and premenstrual dysphoric disorder Another aspect of the invention is a compound of formula I for use in inhibiting the uptake of serotonin in a subject. Preferably that use is in the treatment or prevention in a subject of a disease, disorder or symptom set forth above.

Another aspect of the invention is the use of a compound of formula I in the manufacture of a medicament for inhibiting the uptake of serotonin in a subject. Preferably, the medicament is used for treatment or prevention in a subject of a disease, disorder or symptom set forth above.

In another embodiment, the method of treatment further comprises the step of administering to said patient one or more additional therapeutic agents which, alone or in combination with Compound 1, are effective to treat depression, hypertension, generalized anxiety disorder, phobias, post-traumatic stress syndrome, avoidant personality disorder, sexual dysfunction; eating disorders including bulimia, anorexia nervosa, and binge eating; obesity, chemical dependencies, cluster headache, migraine; pain, including neuropathic pain, diabetic nephropathy, post-operative pain, psychogenic pain disorders, and chronic pain syndrome; Alzheimers disease, obsessive-compulsive disorder, panic disorder with or without agoraphobia, memory disorders, Parkinson's diseases, endocrine disorders, vasospasm, cerebellar ataxia, gastrointestinal tract disorders, negative symptoms of schizophrenia, premenstrual syndrome, Fibromyalgia Syndrome; urinary incontinence, including stress incontinence; Tourette's syndrome, trichotillomania, kleptomania, male impotence, cancer, chronic paroxysmal hemicrania and headache in a mammal, sleep-related breathing disorders, cognitive deficits due to aging, stroke, head trauma, neurodegenerative diseases, schizophrenia, anxiety, aggression and stress, disorders of thermoregulation, respiratory disease, bipolar disorder, psychosis, sleep disorder; mania, including acute mania; bladder disorder, genitourinary disorder, cough, emesis, nausea, psychotic disorders such as paranoia and manic-depressive illness, tic disorder, diabetic cardiomyopathy, diabetic retinopathy, cataracts, myocardial infarction, prolonged fatigue, chronic fatigue, chronic fatigue syndrome, premature ejaculation, dysphoria, post partum depression, social phobia, disruptive behavior disorders, impulse control disorders, borderline personality disorder, attention deficit disorders without hyperactivity, Shy-Drager Syndrome, cerebral ischemia, spinal cord trauma, Huntington's Chorea, amyotrophic lateral sclerosis, AIDS-induced dementia, muscular spasms, convulsions, perinatal hypoxia, hypoxia, cardiac arrest, hypoglycemic neuronal damage, ocular damage and retinopathy, brain edema, tardive dyskinesia, cerebral deficits subsequent to cardiac bypass surgery and grafting, affective disorders, mood disorders, agoraphobia without history of panic disorder, and acute stress disorders; and for reducing the side effects of Compound 1, enhancing or potentiating the activity of Compound 1, or for increasing the duration of pharmacological action of Compound 1.

In yet another embodiment, the method of treatment comprises the further step of administering to said patient one or more therapeutic agents which, alone or in combination with Compound 1, are effective to treat one or more of autism, dyskinesia, disthymic disorder; obesity due to genetic or environmental causes, polycystic ovary disease, craniopharyngeoma, Prader-Willi Syndrome, Frohlich's Syndrome, Type II diabetes, growth hormone deficiency, Turner's Syndrome; pro-inflammatory cytokine secretion or production, jet lag, insomnia, hypersomnia, nocturnal enuresis, restless-legs syndrome, vaso-occlusive events, hyperglycemia, hyperinsulinaemia, hyperlipidaemia, hypertriglyceridemia, diabetes, insulin resistance, impaired glucose metabolism, conditions of impaired glucose tolerance (IGT), conditions of impaired fasting plasma glucose, glomerulosclerosis, syndrome X, coronary heart disease, angina pectoris, vascular restenosis, endothelial dysfunction, impaired vascular compliance, or congestive heart failure; or to increase the onset of action of Compound 1.

In each of the above embodiments, the second therapeutic agent or agents may be administered together with a compound of Formula I as part of a single dosage form or as separate dosage forms. Alternatively, the second therapeutic agent or agents may be administered prior to, consecutively with, or following the administration of a compound of Formula I. In such combination therapy treatment, both the compounds of this invention and the second therapeutic agent(s) are administered by conventional methods. The administration of the second therapeutic agent(s) may occur before, concurrently with, and/or after the administration of the compound of Formula I. When the administration of the second therapeutic agent occurs concurrently with a compound of Formula I, the two (or more) agents may be administered in a single dosage form (such as a composition of this invention comprising a compound of Formula I, a second therapeutic agent or agents as described above, and a pharmaceutically acceptable carrier), or in separate dosage forms. The administration of a composition of this invention comprising both a compound of Formula I and a second therapeutic agent(s) to a subject does not preclude the separate administration of said second therapeutic agent(s), any other therapeutic agent or any compound of this invention to said subject at another time during a course of treatment.

Effective amounts of second therapeutic agent or agents useful in the methods of this invention are well known to those skilled in the art and guidance for dosing may be found in patents referenced herein, as well as in Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the optimal effective-amount range of the additional agent(s).

In one embodiment of the invention where one or more second therapeutic agents are administered to an animal, the effective amount of the compound of Formula I is less than its effective amount would be where the second therapeutic agent(s) are not administered. In another embodiment, the effective amount of the second therapeutic agent is less than its effective amount would be where the compound of Formula I is not administered (i.e., the amount of each second therapeutic agent(s) administered in a monotherapy). In this way, undesired side effects associated with high doses of either agent may be minimized. Other potential advantages (including without limitation improved dosing regimens and/or reduced drug cost) will be apparent to those of skill in the art.

Second therapeutic agents useful in the method of treatment are the same as those described above as part of combination compositions.

According to another aspect, the invention provides a compound of formula I and one or more of the above-described second therapeutic agents, either in a single composition or as separate dosage forms for use in the treatment or prevention in a subject of a disease, disorder or symptom set forth above.

In yet another aspect, the invention provides the use of a compound of formula I and one or more of the above-described second therapeutic agents in the manufacture of a medicament, either as a single composition or as separate dosage forms, for treatment or prevention in a subject of a disease, disorder or symptom set forth above.

The compounds of this invention may be readily assayed for biological activity by known methods. For instance, in vitro methods of determining binding to the serotonin transporter are available using recombinant cell lines, e.g. see Poss M A et. al., U.S. Pat. No. 6,225,324 to Bristol-Myers Squibb; and ex-vivo brain tissue, e.g. see Young J W et. al., U.S. Pat. No. 5,648,396 to Sepracor; and Habert E et. al., Eur. J. Pharmacol 1985 118: 107.

Animal models of depression provide reproducible read-outs that correlate with human clinical response to antidepressant drugs, including serotonin reuptake inhibitors and specifically Compound 1. For instance, see Porsolt R D et. al., Eur. J. Pharmacol. 1979 57: 201; Detke M J et. al., Psychopharmacology 1995 121: 66; *"Drug Discovery and Evaluation"*, Vogel H G and Vogel W H (eds.), p. 304, 1997, Springer-Verlag, New York; and El Yacoubi M et. al., Proc. Natl. Acad. Sci. USA 2003 100: 6227; for descriptions of the well-known forced swim test and tail suspension test. Each of the compounds of this invention may be tested in such animal models.

The rate of metabolism of compounds of this invention may be determined and compared to that of Compound 1 in the presence, for instance, of heterologously expressed CYP2D6, or human liver microsomes (both available from BD Gentest, Woburn, Mass.). The compounds may also be tested in whole animals e.g. by oral or parenteral administration, measuring the disappearance of the administered compound and, if desired, the appearance of metabolites. Means for such measurements are well known, e.g. see Segura M et. al., Rapid Commun. Mass Spectrom. 2003 17: 1455; and Hartter S et. al., Ther. Drug Monit. 1994 16: 400. The inactivation of CYP2D6 by compounds of this invention may also be measured by known means to determine relevant enzymatic parameters such as $k_{INACT}$. See for instance Bertelsen K M et. al., Drug Metab. Dispos. 2003 31: 289. The effects of a compound of formula I on other drugs known to be metabolized by cytochrome 2D family enzymes may also be measured and compared to the corresponding effects caused by Compound 1; e.g. see Hashimoto K et. al., Eur. J. Pharmacol. 1993 228: 247. This interaction may be measured after either a single doses of compound I and a compound of Formula I, or after repeated doses to measure cumulative cytochrome inactivation.

Diagnostic Methods and Kits

According to another embodiment, the invention provides a method of determining the concentration of Compound 1 in a biological sample, said method comprising the steps of:
a) adding a known concentration of a second compound to said biological sample, said second compound having the formula:

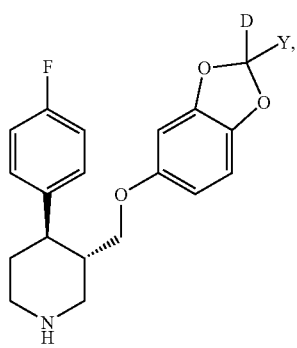

(I)

or a salt thereof, wherein:
D is deuterium;
each Y is independently selected from deuterium or hydrogen;
each hydrogen atom is optionally substituted by deuterium; and each carbon atom is optionally substituted by $^{13}C$ b) subjecting said biological sample to a measuring device that distinguishes Compound 1 from said second compound;
c) calibrating said measuring device to correlate the detected quantity of Compound 1 with the known concentration of said second compound added to said biological sample; and
d) determining the concentration of said compound in said biological sample by comparing the detected quantity of Compound 1 with the detected quantity and known concentration of said second compound.

Measuring devices that can distinguish Compound 1 from said second compound include any measuring device that can distinguish between two compounds that are of identical structure except that one contains one or more heavy atom isotope versus the other. Preferably, such a measuring device is a mass spectrometer.

In a preferred embodiment, at least three combined hydrogen atoms and carbons are, respectively, deuterium and $^{13}C$ in said second compound; i.e. (total number of D)+(number of $^{13}C$)$\geq$3.

In another preferred embodiment, the method comprises the additional step of separating both Compound 1 and said second compound from said biological sample by organic or solid phase extraction prior to step b).

Compound 1 and the second compound will have similar solubility, extraction, and chromatographic properties, but significantly different molecular mass. Thus, the second compound is useful as an internal standard in a method that comprises the step of organic or solid phase extraction to measure the efficiency of that extraction and to ensure an accurate determination of the true concentration of Compound 1 (see Tuchman M and McCann M T, Clin. Chem. 1999 45: 571; Leis H J et. al., J. Mass Spectrom. 2001 36: 923; Taylor R L et. al., Clin. Chem. 2002 48: 1511).

The compounds of the present invention (the second compound) are particularly useful in this method since they are not radioactive and therefore do not pose a hazard to personnel handling the compounds. Thus, these methods do not require precautions beyond those normally applied in clinical sample analysis.

Furthermore, stably labeled isotopes have long been used to assist in research into the enzymatic mechanism of cytochrome P450 enzymes (e.g. Korzekwa K R et. al., Drug Metab. Rev. 1995 27: 45 and references therein; Kraus J A and Guengerich F P, J. Biol. Chem. 2005 280: 19496; Mitchell K H et. al., Proc. Natl. Acad. Sci. USA 2003 109: 3784).

In another embodiment, the invention provides a diagnostic kit comprising a) one or more diagnostic compounds having the formula I,

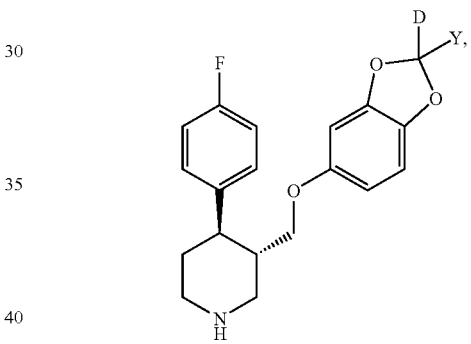

or an salt thereof, wherein:
D is deuterium;
each Y is independently selected from hydrogen or deuterium;
each hydrogen atom is optionally substituted by deuterium; and each carbon atom is optionally substituted by $^{13}C$; and b) instructions for using said compound to determine the concentration of a test compound in a biological sample.

In another embodiment, the invention provides a method of evaluating the metabolic stability of a compound of formula I, comprising the steps of contacting the compound of formula I or its acid addition salt with a metabolizing enzyme source for a period of time; and comparing the amount of said compound and metabolic products of said compounds after said period of time.

In one preferred embodiment, the method comprises an additional step of comparing the amount of said compound and said metabolic products of said compounds at an interval during said period of time. This method allows the determination of a rate of metabolism of said compound.

In another preferred embodiment, the method comprises the additional steps of contacting a compound of formula I with said metabolizing enzyme source; comparing the amount of said compound of formula I and metabolic products of said compound of formula I after said period of time determining a rate of metabolism of said compound of formula I; and comparing the metabolic stability of Compound 1 and said compound of formula I. This method is useful in determining whether and at which sites on a compound of formula I additional deuterium or $^{13}$C substitution would cause increases in metabolic stability. It is also useful in comparing the metabolic stability of a compound of formula I with the metabolic stability of Compound 1.

A metabolizing enzyme source may be a purified, isolated or partially purified metabolic protein, such as a cytochrome P450; a biological fraction, such as a liver microsome fraction; or a piece of a metabolizing organ, such as hepatocytes or a liver slice.

The determination of the amount of compound and its metabolic products is well known in the art. It is typically achieved by removing an aliquot from the reaction mixture and subjecting it to an analysis capable of distinguishing between the compound and its metabolites, such as reversed-phase HPLC with UV absorption or mass spectroscopic detection. Concentrations of both the metabolizing enzyme and the compound may be varied to determine kinetic parameters, for instance, by using appropriate nonlinear regression software such as is known in the art. By comparing the kinetic parameters of both a compound of formula I and Compound 1 an apparent steady-state deuterium isotope effect ($^D$(V/K)) can be determined as the ratio of products formed in the hydrogen versus deuterium reactions.

The determination of a rate of metabolism of a compound of formula I may be achieved in a reaction separate from the reaction for determining the metabolism rate of Compound 1. Alternatively, Compound 1 may be admixed with a compound of formula I in a competition experiment to determine rates of disappearance of the two compounds, making use of analytical instrumentation capable of differentiating between the two compounds based on their mass differences.

In yet another embodiment, pre-steady state kinetics, such as $V_0$, may be determined by means known in the art, for instance, using quench-flow apparatus, by monitoring the quenched reactions at varying times after mixing the compound or isotopologue with the metabolizing enzyme source.

In a related embodiment, the invention provides a kit comprising, in separate vessels: a) Compound 1; and b) a metabolizing enzyme source. The kit is useful for comparing the metabolic stability of a compound of formula I with Compound 1, as well as evaluating the effect of deuterium and $^{13}$C replacement at various positions on a compound of formula I. In a preferred embodiment, the kit further comprises instructions for using Compound 1 and said metabolizing enzyme source to evaluate the metabolic stability of a compound of formula I.

In order that the invention might be more fully understood, the following examples are set forth. They are not intended to limit the scope of the invention and further examples will be evident to those of ordinary skill in the art. In each example set forth herein, carbon shall be $^{12}$C, and hydrogen shall by $^1$H, each incorporated at its natural abundance, unless otherwise specified.

EXAMPLE 1

Deuterodibromomethane. A solution of 1.1 mole of sodium deuteroxide in 140 mL of deuterium oxide is treated under argon with 116 mmol of arsenious oxide to form a solution of sodium arsenite. Bromoform (190 mmol) is treated under argon with 6.5 mL of ethanol-d (CH$_3$CH$_2$OD) and 1 mL of the sodium arsenite solution and warmed briefly (heat gun) to initiate reaction. The remainder of the sodium arsenite solution is added via dropping funnel at a rate to maintain gentle reflux, then the mixture is heated in a 100° C. oil bath for an additional 4.5 h. The mixture is azeotropically distilled, then the distillate is separated and the aqueous layer extracted with 15 mL of pentane. The organic layers are combined, dried over CaCl$_2$, and distilled to yield the title compound.

EXAMPLE 2

2-deuterobenzo[d][1,3]dioxole-5-carbaldehyde (Formula V wherein Y=H and R=formyl). A solution of 3,4-dihydroxybenzaldehyde (20 mmol) in 60 mL of dimethylformamide (DMF) is treated under argon with 60 mmol of the product of example 1 and 70 mmol of CsF. The mixture is heated in a 140° C. oil bath for 3 h with vigorous stirring. The mixture is then filtered, concentrated in vacuo, and the residue is purified by silica gel flash chromatography (ether/hexanes eluant), yielding the title product.

EXAMPLE 3

2-deuterobenzo[d][1,3]dioxol-5-yl formate. A 13.4 mL portion of acetic anhydride is warmed under an argon atmosphere in a 40° C. bath and treated, during 6 h in 3 equal portions, with 10 mmol of 50% hydrogen peroxide. The solution is treated with 10 mmol of the product of example 2, and reaction is allowed to proceed for 2 h at about 40° C. The solvents are removed in vacuo and the residue purified by Kugelrohr distillation at about 2 mm Hg to yield the title product.

EXAMPLE 4

2-deuterobenzo[d][1,3]dioxol-5-ol (Formula II wherein Y=H). A 6.4 mmol portion of the product of example 3 is dissolved in 2 mL of methanol and the mixture is treated with 21 µL of acetic acid, then heated under reflux for 15 h. The solution is concentrated in vacuo and the residue is Kugelrorh distilled (ca. 2 mm Hg) to yield the title compound.

EXAMPLE 5

2-dideuterobenzo[d][1,3]dioxole-5-carbaldehyde (Formula V wherein Y$_1$=D and R=formyl). 3,4-Hydroxybenzaldehyde (Formula IV wherein R=formyl, 10.35 g, 75 mmol), DMF (450 ml), Cs$_2$CO$_3$ (33 g, ~100 mmol) and dideuterodibromomethane (99.6% atom D, 15 g, ~85 mmol) were mixed at 130-140° C. 1 h. The reaction mixture was cooled down, filtered off and the filtrate was evaporated. The residual oil was dissolved in ethyl acetate and washed with water, brine and dried MgSO4. The crude product was isolated as a brown oil which crystallized upon refrigeration, yielding the title product (10.5 g).

EXAMPLE 6

2-dideuterobenzo[d][1,3]dioxol-5-ol (Formula II wherein Y$_1$=D). The crude product from Example 5 (10.5 g, ~75 mmol) was dissolved in 380 ml DCM followed by the addition of 30% H$_2$O$_2$ (20 ml) and formic acid (12 ml). The reaction mixture was vigorously stirred under refluxed for 24 h. The volatiles were evaporated and the residue was treated with 250 ml 2M NaOH. The crude title product was extracted with ether, dried over MgSO$_4$, and purified on silica using chloroform as eluent. (3.2 g, 30%).

EXAMPLE 7

(3S,4R)-benzyl 3-((2-deuterobenzo[d][1,3]dioxol-5-yloxy)methyl)-4-(4-fluorophenyl)piperidine-1-carboxylate (Formula III wherein Y=H and W is benzyloxycarbonyl). A solution of 2.7 mmol of the product of example 4 in 10 mL of acetone is treated with 4 mmol of finely ground cesium carbonate, followed by 2.7 mmol of (3S,4R)-benzyl 4-(4-fluorophenyl)-3-((methylsulfonyloxy)methyl)piperidine-1-carboxylate (Sugi K et. al. U.S. Pat. No. 6,476,227 to Sumika). The mixture is heated under reflux for about 8 h, then cooled, filtered, and concentrated in vacuo. The residue is partitioned between ethyl acetate and water, the organic layer is washed with brine, dried, and concentrated in vacuo. This residue is used in subsequent reactions without further purification.

EXAMPLE 8

(3S,4R)-3-((2-deuterobenzo[d][1,3]dioxol-5-yloxy)methyl)-4-(4-fluorophenyl)piperidine hydrochloride (Formula I wherein Y=H). The entire yield of Example 8, except for an approximately 2 mg retained sample, is dissolved in 8 mL of ethanol, treated with a catalytic amount of 10% Pd on carbon (spatula tip) and stirred under an atmosphere on hydrogen (balloon) for about 16 h. The mixture is filtered and concentrated, and the residue taken up in toluene and again concentrated. The residue is dissolved in about 2.5 mL of dry isopropanol and treated with hydrogen chloride gas to form a white precipitate. Excess HCl is blown off by bubbling an argon stream into the solution for about 3 min, then the mixture is filtered, washing with a small amount of isopropanol, yielding the title product.

EXAMPLE 9

(3S,4R)-benzyl 3-((2,2-dideuterobenzo[d][1,3]dioxol-5-yloxy)methyl)-4-(4-fluorophenyl)piperidine-1-carboxylate (Formula III wherein Y=H and W is benzyloxycarbonyl). An 11.1 mmol portion of the product of Example 7 is reacted with (3S,4R)-benzyl 4-(4-fluorophenyl)-3-((methylsulfonyloxy)methyl)piperidine-1-carboxylate according to the general procedure set forth in Example 8 to yield the crude product which, on purification by silica gel chromatography using ethyl acetate/hexanes eluant, gives the title compound.

EXAMPLE 10

(3S,4R)-3-((2-deuterobenzo[d][1,3]dioxol-5-yloxy)methyl)-4-(4-fluorophenyl)piperidine hydrochloride (Formula I wherein Y=D). Hydrogenation of a 6.8 mmol portion of the product of Example 10 and hydrochloride salt formation according to the general procedure set forth in Example 9 yields the title compound.

EXAMPLE 11

(3S,4R)-tert-butyl 4-(4-fluorophenyl)-3-(hydroxymethyl) piperidine-1-carboxylate. A 6.7 mmol portion of (3S,4R)-benzyl 4-(4-fluorophenyl)-3-(hydroxymethyl)piperidine-1-carboxylate (U.S. Pat. No. 6,476,227) is dissolved in 25 mL of dioxane and treated under argon with 7.1 mmol of di-tert-butyl dicarbonate and 200 mg of 10% Pd/C. The mixture is hydrogenated under an atmosphere of hydrogen (balloon) for about 17 h, then filtered and concentrated in vacuo. The residue is purified by silica gel chromatography (methanol/methylene chloride eluant), yielding the title product.

EXAMPLE 12

(3S,4R)-tert-butyl 4-(4-fluorophenyl)-3-formylpiperidine-1-carboxylate. A solution of 6.5 mmol of oxalyl chloride in 15 mL of methylene chloride is cooled under argon in a CO$_2$/acetone bath and treated dropwise with 13 mmol of dimethylsulfoxide. To this mixture is added, during about 10 min, a solution of 5.8 mmol of the product of example 12 as a solution in 6 mL of methylene chloride. The resulting solution is stirred for 1.5 h, then treated with 15 mmol of triethylamine. After an additional 15 min the cold bath is removed and stirring is continued an additional 45 min. The reaction mixture is partitioned between ether and saturated NH$_4$Cl (40 mL each), and the organic layer is washed with water and brine, dried over MgSO$_4$, and concentrated in vacuo to yield the title product, which is used without subsequent purification.

EXAMPLE 13

(3S,4R)-1-(tert-butoxycarbonyl)-4-(4-fluorophenyl)piperidine-3-carboxylic acid. One half of the product of Example 13 is dissolved in 12 mL of tert-butyl alcohol and 4 mL of water and 3.3 mmol of KMnO$_4$ are added. The mixture is stirred for 4 h at room temperature, then filtered, washing the solids with water. The mixture is concentrated to about 5 mL in vacuo, and partitioned between 40 mL of ether and 3×10 mL of 1 N NaOH. The aqueous layers are combined, cooled in an ice bath, rendered acidic with saturated KHSO$_4$, and extracted with methylene chloride (3×). These organic layers are combined, washed with 50% brine, dried over MgSO$_4$, and concentrated in vacuo, yielding the title compound.

EXAMPLE 14

(3S,4R)-tert-butyl 3-(dideutero(hydroxy)methyl)-4-(4-fluorophenyl)piperidine-1-carboxylate (Formula VI wherein W=tert-butoxycarbonyl and the hydroxymethyl carbon is disubstituted with deuterium). A solution of 3.7 mmol of the product of Example 13 are dissolved in 25 mL of methylene chloride, cooled in an ice bath, and treated with 3.9 mmol of oxalyl chloride and 2 drops of dimethylformamide. The ice bath is removed and the mixture is stirred for about 2.5 h, then concentrated in vacuo. The crude acid chloride is dissolved in 20 mL of ethyl acetate and treated with 7.4 mmol of sodium borodeuteride (Aldrich). The mixture is stirred for 4 h, then cooled in an ice bath and treated dropwise with about 1 mL of 5% KHSO$_4$ solution. More ethyl acetate is added and the solution is extracted with 5% KHSO$_4$, saturated NaHCO$_3$, and brine, then dried over MgSO$_4$ and concentrated in vacuo. Silica gel chromatography (methanol/methylene chloride eluant) yields the title product.

EXAMPLE 15

(3S,4R)-tert-butyl 3-((2,2-dideuterobenzo[d][1,3]dioxol-5-yloxy)dideuteromethyl)-4-(4-fluorophenyl)piperidine-1-carboxylate (Formula III wherein Y=D, W=tert-butoxycarbonyl, and both hydrogens on the piperidine-3-methylene carbon are substituted by deuterium). A 1.2 mmol sample of the product of Example 7 is reacted with the product of Example 15 according to the general procedure set forth in Example 8 to yield the crude product which is purified by silica gel chromatography, using ethyl acetate/hexanes eluant, to yield the title compound.

EXAMPLE 16

(3S,4R)-3-((2,2-dideuterobenzo[d][1,3]dioxol-5-yloxy) dideuteromethyl)-4-(4-fluorophenyl)piperidine hydrochloride (Formula I wherein Y=D and both hydrogens on the piperidine-3-methylene carbon are substituted by deuterium. A 0.87 mmol portion of the product of Example 16 is dissolved in 3 mL of isopropanol, cooled in an ice/water bath under argon, and treated with a slow hydrogen chloride gas stream for about 2 min. The mixture is capped and allowed to stand for 1 hr, then argon is bubbled through the solution for 2 min to blow off excess HCl. The mixture is filtered, washing the filtrate with a small amount of cold isopropanol, yielding the title compound.

EXAMPLE 17

(3R,4R)-4-(4-fluoro-2,3,5,6-tetradeuterophenyl)-1-methylpiperidine-3-carboxylic acid, (2,10)-camphorsultamyl amide. A mixture of 9.4 mmol of Mg turnings in 2 mL of THF is treated with a catalytic amount of iodine (small crystal) and heated in an argon atmosphere under reflux for 30 min. The resulting mixture is treated during 20 min with a solution of 8.5 mmol of 4-fluoro-2,3,5,6-tetradeuterobromobenzene (C/D/N isotopes) in 1.5 mL of THF. The mixture is stirred for an additional 2 h under reflux, then cooled to room temperature. A 7.6 mmol portion of 1-methyl-1,2,5,6-tetrahydropyridine-3-carboxylic acid, (2,10)-camphorsultamyl amide (U.S. Pat. No. 5,962,689) in 30 mL of toluene is cooled in an ice/salt bath under argon, and treated during 20 min with the Grignard reagent prepared above. The mixture is stirred in the cold for 17 h, then quenched with saturated ammonium chloride. The aqueous layer is washed with ethyl acetate and the combined organic layers are washed with water and then brine, dried over $MgSO_4$, and concentrated in vacuo. Silica gel chromatography using ethyl acetate eluant provides the title compound.

EXAMPLE 18

(3S,4R)-methyl 4-(4-fluoro-2,3,5,6-tetradeuterophenyl)-1-methylpiperidine-3-carboxylate. A 1.7 mmol sample of the product of Example 18 is dissolved in 5 mL of toluene and treated with 2 5 mmol of finely ground potassium tert-butoxide and stirred under argon at room temperature for 1 h. Methanol (1 mL) is added and stirring is continued for 5 h, then the mixture is diluted with toluene and washed with water and brine, dried, and concentrated in vacuo. The residue is purified by silica gel chromatography using acetone/chloroform eluant to give the title product.

EXAMPLE 19

((3S,4R)-4-(4-fluoro-2,3,5,6-tetradeuterophenyl)-1-methylpiperidin-3-yl)methanol (Formula VI wherein W is methyl and each hydrogen on the phenyl ring is substituted with deuterium). A 3.7 mmol portion of the product of Example 19 is dissolved in 5 mL of THF and added dropwise to a cold (ice bath) solution of 5.5 mL of 1 M $LiAlH_4$ in THF during 15 min. The mixture is stirred in the cold for 10 min, then at room temperature for 3 h. The mixture is again cooled and the excess $LiAlH_4$ is quenched by sequential addition of 0.21 mL of water, 0.21 mL of 15% aqueous NaOH, and 0.63 mL of water. The resulting suspension is filtered through celite and concentrated in vacuo, and purified by preparative reversed-phase HPLC (water/$CH_3CN$ gradient with 0.1% TFA) to yield, after formation of the free base (ethyl acetate/saturated $NaHCO_3$ wash), the title compound.

EXAMPLE 20

(3S,4R)-3-((2,2-dideuterobenzo[d][1,3]dioxol-5-yloxy) methyl)-4-(4-fluoro-2,3,5,6-tetradeuterophenyl)-1-methylpiperidine hydrochloride (Formula III wherein Y is deuterium, W is methyl, and each hydrogen on the phenyl ring is substituted with deuterium). A 2.2 mmol sample of the product of Example 20 is dissolved in 4 mL methylene chloride and cooled in an ice/salt bath under argon. The solution is treated during 15 min with 2.3 mmol of methanesulfonyl chloride in 1.5 mL of methylene chloride. The mixture is stirred for 1.5 h in the cold, then concentrated in vacuo. The residue is triturated with isopropyl ether 2× and the resulting solid is partitioned between ether and saturated $NaHCO_3$. The ether layer is washed with brine, dried over $MgSO_4$, concentrated in vacuo and the resulting methanesulfonate free base is used immediately for subsequent reaction. A 2.7 mmol sample of the product of Example 7 is dissolved in 4 mL of DMF and treated with 1.35 mmol of $Cs_2CO_3$ as a 20% aqueous solution. The mixture is concentrated in vacuo, treated with 4 mL of DMF, again concentrated in vacuo, and treated with 3 mL of DMF. The entire yield of the above-formed methanesulfonate, save a retained sample of about 3 mg, is dissolved in 3 mL of DMF and added to the DMF solution of the cesium salt. The mixture is stirred for 16 h at room temperature, then concentrated in vacuo. The residue is partitioned between ether and 2N NaOH (2×), the organic layer is washed with water and then brine, dried over $MgSO_4$, filtered, and treated with 2.5 mmol of anhydrous HCl as a 1 M solution in ether. The resulting hydrochloride is filtered, dried, and used directly in subsequent reaction.

EXAMPLE 21

(3S,4R)-phenyl 3-((2,2-dideuterobenzo[d][1,3]dioxol-5-yloxy)methyl)-4-(4-fluoro-2,3,5,6-tetradeuterophenyl)piperidine-1-carboxylate (Formula III wherein Y is deuterium, W is phenyl carbamate, and each hydrogen on the phenyl ring is substituted with deuterium). A 1.4 mmol sample of the product of Example 21 is dissolved in 3 mL of methylene chloride and cooled under argon in an ice/water bath. The mixture is treated dropwise with 1.54 mmol of phenyl chloroformate during 5 min. The cold bath is removed and the mixture is stirred for 17 h at room temperature. The reaction mixture is partitioned between 15 mL each of ether and saturated $NaHCO_3$, and the organic layer is washed with 10% $KHSO_4$, water, and brine, then dried over $MgSO_4$ and concentrated in vacuo. Silica gel chromatography using ethyl acetate/hexanes eluant provides the title compound.

EXAMPLE 22

(3S,4R)-3-((2,2-dideuterobenzo[d][1,3]dioxol-5-yloxy) methyl)-4-(4-fluoro-2,3,5,6-tetradeuterophenyl)piperidine hydrochloride (Formula I wherein Y is deuterium, and each hydrogen on the phenyl ring is substituted with deuterium). 0.8 mmol of the product of Example 22 is suspended in 0.37 mL of 3 N KOH and the mixture is heated under reflux for 4 h. The mixture is cooled, and partitioned between 10 mL each water and methylene chloride. The aqueous portion is extracted again with methylene chloride and the combined organic layers are washed with 50% brine, dried over $MgSO_4$ and concentrated in vacuo. The residue is taken up in 2 mL of isopropanol and treated with 0.9 mmol of anhydrous HCl as a 4.2 N solution in dioxane. The resulting solid is filtered, washed with a small amount of isopropanol, then with ether, and dried to yield the title compound.

EXAMPLE 23

Inhibition of serotonin uptake. Activity of test compounds in inhibiting uptake of [$^3$H]-serotonin in recombinant cells expressing the human serotonin transporter is conducted by MDS Pharma Services using essentially the protocol of Gu H et. al., J. Biol. Chem. 1994 269: 7124, using vehicle as a negative control and fluoxetine as a positive control. This test demonstrates low or sub-nanomolar activity of each tested compound of formula I.

EXAMPLE 24

In vivo antidepressant effects. The product of Example 11 is tested at MDS Pharma by oral administration to mice (n=8) to determine its effect on total immobility time during forced tail suspension, using essentially the procedure of "*Drug Discovery and Evaluation*", Vogel H G and Vogel W H (eds.), p. 304, 1997, Springer-Verlag, New York. A 15 mg/kg dose of the product of Example 11 (calculated as the free base) causes a statistical reduction in immobility time versus vehicle control animals.

EXAMPLE 25

(3S, 4R)-trans-3-carboxy-4-(4-fluorophenyl)-N-methylpiperidine (Formula VII wherein W=methyl). (3S, 4R)-trans-3-hydroxymethyl-4-(4-fluorophenyl)-N-methylpiperidine (5 g, 22 4 mmol) was treated with a slurry of Dowex 50WX-400 (200 ml) in water until dissolution. To the mixture, $CrO_3$ (9 g, 90 mmol) in 20 ml water was added in one portion and the Dowex slurry was mixed at 60° C. for 6 h. The resin was filtered off and washed three times with distilled water (discard), and five times with a TEA/MeOH/water mixture (1/3/7). The basic washes were combined and evaporated to give 3.7 g (70%) of the title compound as a brown solid.

EXAMPLE 26

(3S, 4R)-trans-3-carbomethoxy-4-(4-fluorophenyl)-N-methylpiperidine (Formula VIII wherein W=methyl). The product from Example 25 (7.5 g, 32 mmol) was dissolved in MeOH (200 ml), cooled down below −20° C. and treated with $SOCl_2$ (10 ml, 140 mmol). The reaction mixture was refluxed for 3 h and the volatiles were removed under reduced pressure. The residue was treated with toluene and 5% $NaHCO_3$ aq in a separatory funnel. The organic layer was washed with brine, dried over $MgSO_4$ and evaporated to give the title compound as an oil (quantitative).

EXAMPLE 27

(3S, 4R)-trans-3-dideuterohydroxymethyl-4-(4-fluorophenyl)-N-methylpiperidine (Formula VI wherein W=methyl and $Y_2=Y_3=D$). 1M $LiAlD_4$ in THF (96 atom % D, 25 ml) was diluted with dry THF (50 ml) and cooled down to −50° C. A solution of the compound from example 27 (5.5 g, 22 mmol) in 10 ml THF was slowly added to the reaction vessel over 30 min maintaining the temperature below −30° C. The reaction mixture was allowed to warm up to room temperature and kept overnight. The excess of $LiAlD_4$ was decomposed by the addition of 1.5 ml water. The solid was filtered off and washed with ethyl acetate. The combined filtrate layers were evaporated, the residue dissolved in toluene (100 ml), washed with 5% $NaHCO_3$, and dried over $MgSO_4$. The solvent was removed under reduced pressure to provide the title compound which was recrystallized (4 g, 80%) using hexane-toluene (9/1).

EXAMPLE 28

(3S, 4R)-trans-3-dideuterohydroxymethyl-4-(4-fluorophenyl)-N-methylpiperidine mesylate (Formula IX wherein W=methyl and $Y_2=Y_3=D$). The product from Example 27 (2.25 g, 10 mmol) was dissolved in 20 ml dichloroethane followed by the addition of methanesulfonylchloride (1.2 g, 10.5 mmol). The reaction mixture was kept at room temperature 3 h and the volatiles were removed under reduced pressure to provide the title compound in quantitative yield.

EXAMPLE 29

(3S,4R)-3-((2,2-dideuterobenzo[d][1,3]dioxol-5-yloxy)dideuteromethyl)-4-(4-fluorophenyl)-N-methylpiperidine (Formula III wherein W=methyl and $Y_1=Y_2=Y_3=D$). The compound of Formula II from example 7 (10 mmol, 1.4 g) was dissolved in 50 ml toluene followed by addition of 3M NaOH (25 ml), tetraoctylammonium bromide (0.5 mmol, 275 mg) and the compound from Example 28 (10 mmol). The reaction mixture was stirred with heating (80-100° C.) for 4 h, cooled down, diluted with water (100 ml) and toluene (50 ml). The organic layer was separated, washed with 5% $NaHCO_3$, brine and dried over $MgSO_4$, filtered and concentrated to provide the title compound as a solid residue that was used in the next step.

EXAMPLE 30

(3S,4R)-3-((2,2-dideuterobenzo[d][1,3]dioxol-5-yloxy)dideuteromethyl)-4-(4-fluorophenyl)-N-(4-nitrophenoxycarbonyl)piperidine (Formula III wherein W=4-nitrophenyloxycarbonyl and $Y_1=Y_2=Y_3=D$). The product from Example 29 (~10 mmol) was dissolved in 70 ml toluene, followed by addition of DIEA (~2 mmol, 0.4 ml) and 4-nitrophenyl chloroformate (10 mmol, 2 g). The reaction mixture was stirred at 80° C. for 2 h, diluted with toluene (+50 ml) washed with water twice, and evaporated to provide the title compound.

EXAMPLE 31

(3S,4R)-3-((2,2-dideuterobenzo[d][1,3]dioxol-5-yloxy)dideuteromethyl)-4-(4-fluorophenyl)piperidine hydrochloride (Formula I wherein $Y_1=Y_2=Y_3=D$). The product from Example 30 (~10 mmol) was dissolved in 70 ml dioxane followed by addition of 2M NaOH (100 ml). The reaction mixture was stirred at 70° C. for 3 h. The volatiles were evaporated and the residue was distributed between ether and water. The organic layer was washed with 1M NaOH, brine and dried over $MgSO_4$. After filtration, the solvent was removed under reduced pressure. The residual oil was dissolved in 15 ml acetic acid and loaded on to RP C-18 column (50×300). Prep HPLC was performed at 50 ml/min, in a water-acetonitrile system with 0.1% TFA as ion-pairing agent. The fractions containing target compound in sufficient purity were collected, evaporated up to solid. The residue was dissolved in a small volume of acetone and precipitated with a mixture of 1M HCl in ether/hexane two times. The solid salt was dried overnight under high vacuum to provide the title compound (1.58 g, 40%).

EXAMPLE 32

(3S, 4R)-trans-3-hydroxymethyl-4-(4-fluorophenyl)-N-methylpiperidine mesylate (Formula IX wherein W=methyl). (3S, 4R)-trans-3-hydroxymethyl-4-(4-fluorophenyl)-N-methylpiperidine was reacted as described for Example 28 to provide the title compound.

EXAMPLE 33

(3S,4R)-3-((2,2-dideuterobenzo[d][1,3]dioxol-5-yloxy)methyl)-4-(4-fluorophenyl)-N-methylpiperidine (Formula III wherein W=methyl and $Y_1$=D). The product from example 7 (10 mmol, 1.4 g) was dissolved in 50 ml toluene followed by addition of 3M NaOH (25 ml), tetraoctylammonium bromide (0.5 mmol, 275 mg) and the product from example 32 (10 mmol). The reaction mixture was stirred with heating (80-100° C.) for 4 h, cooled down, diluted with water (100 ml) and toluene (50 ml). The organic layer was separated, washed with 5% $NaHCO_3$, brine and dried over $MgSO_4$ to provide the title compound as a solid residue was used in the next step after evaporation.

EXAMPLE 34

(3S,4R)-3-((2,2-dideuterobenzo[d][1,3]dioxol-5-yloxy)methyl)-4-(4-fluorophenyl)-N-(4-nitrophenoxycarbonyl)piperidine (Formula III wherein W=4-nitrophenyloxycarbonyl and $Y_1$=D). The product from Example 33 was reacted as described for Example 30 to provide the title compound.

EXAMPLE 35

(3S,4R)-3-((2,2-dideuterobenzo[d][1,3]dioxol-5-yloxy)methyl)-4-(4-fluorophenyl)piperidine hydrochloride (Formula I wherein $Y_1$=D). The product from Example 34 was reacted as described for Example 31 to provide the title compound.

EXAMPLE 36

Microsomal Assay

Certain in vitro liver metabolism studies have been described previously in the following references, each of which is incorporated herein in their entirety: Obach, R. S. Drug Metab Disp 1999, 27, p. 1350 "Prediction of human clearance of twenty-nine drugs from hepatic microsomal intrinsic clearance data: An examination of in vitro half-life approach and nonspecific binding to microsomes"; Houston, J. B. et al., Drug Metab Rev 1997, 29, p. 891 "Prediction of hepatic clearance from microsomes, hepatocytes, and liver slices"; Houston, J. B. Biochem Pharmacol 1994, 47, p. 1469 "Utility of in vitro drug metabolism data in predicting in vivo metabolic clearance"; Iwatsubo, T et al., Pharmacol Ther 1997, 73, p. 147 "Prediction of in vivo drug metabolism in the human liver from in vitro metabolism data"; and Lave, T. et al., Pharm Res 1997, 14, p. 152 "The use of human hepatocytes to select compounds based on their expected hepatic extraction ratios in humans".

The objectives of the present study were to determine the metabolic stability of the test compounds in pooled liver microsomal incubations and to perform full scan LC-MS analysis for the detection of major metabolites. Samples of the test compounds, exposed to pooled human liver microsomes, were analyzed using HPLC-MS (or MS/MS) detection. For determining metabolic stability, multiple reaction monitoring (MRM) was used to measure the disappearance of the test compounds. For metabolite detection, Q1 full scans were used as survey scans to detect the major metabolites.

Experimental Procedures: Human liver microsomes were obtained from Absorption Systems L. P. (Exton, Pa.). Details about the matrices used in the experiments are shown in the table below. The incubation mixture was prepared as follows:

| Reaction Mixture Composition | |
| --- | --- |
| Liver Microsomes | 1.0 mg/mL |
| NADPH | 1 mM |
| Potassium Phosphate, pH 7.4 | 100 mM |
| Magnesium Chloride | 10 mM |
| Test Compound | 1 μM |

Incubation of Test Compounds with Liver Microsomes: The reaction mixture, minus cofactors, was prepared. An aliquot of the reaction mixture (without cofactors) was incubated in a shaking water bath at 37° C. for 3 minutes. Another aliquot of the reaction mixture was prepared as the negative control. The test compound was added into both the reaction mixture and the negative control at a final concentration of 1 μM. An aliquot of the reaction mixture was prepared as a blank control, by the addition of plain organic solvent (not the test compound). The reaction was initiated by the addition of cofactors (not into the negative controls), and then incubated in a shaking water bath at 37° C. Aliquots (200 μL) were withdrawn in triplicate at 0, 15, 30, 60, and 120 minutes and combined with 800 μl, of ice-cold 50/50 acetonitrile/deionized water to terminate the reaction. The positive controls, testosterone and propranolol, were run simultaneously with the test compounds in separate reactions. All samples were analyzed using LC-MS (or MS/MS). An LC-MRM-MS/MS method was used for metabolic stability. Also, Q1 full scan LC-MS methods were performed on the blank matrix and the test compound incubation samples. The Q1 scans served as survey scans to identify any sample unique peaks that might represent the possible metabolites. The masses of these potential metabolites can be determined from the Q1 scans.

Results: Metabolic Stability:

TABLE 2

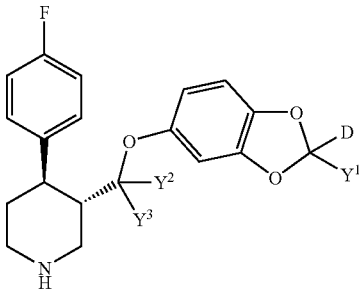

| | | | | % Remaining | | |
| --- | --- | --- | --- | --- | --- | --- |
| Example | Y1 | Y2 | Y3 | 30 min | 60 min | 120 min |
| Paroxetine | No deuterium | | | 51 | 51 | 44 |
| A | D | H | H | 29 | 26 | 16 |
| B | D | D | D | 22 | 10 | 6 |

The test compounds were evaluated in the human liver microsome assay described above along with paroxetine as a control. The columns of Table 2 labelled "% remaining" refer to the percentage of each test compound remaining after 30, 60 and 120 minute intervals in the human microsomal assay.

As seen from Table 2, above, paroxetine exhibited relative stability in the microsome assay, which is consistent with the compound being an irreversible inhibitor of the CYP2D6 enzyme. By contrast, the deuterated analogs of the invention displayed appreciable degradation over time. The results indicate that deuterated compounds according to the invention may exhibit beneficial properties when administered to patients, e.g., for patients where irreversible inhibition of the cytochrome is undesirable.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated compound of formula I:

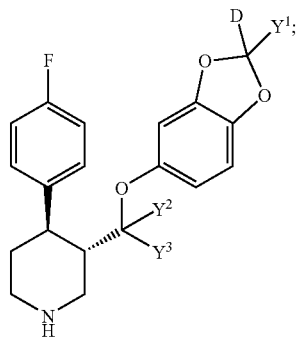

or a pharmaceutically acceptable salt thereof; wherein:
D is deuterium;
$Y^1$ is deuterium;
each of $Y^2$ and $Y^3$ are independently selected from deuterium and hydrogen; and
each hydrogen is independently optionally replaced with deuterium; and
wherein at least 90% of the compound has a deuterium atom at each position designated as deuterium in formula I.

2. The isolated compound according to claim 1, wherein up to 4 hydrogen atoms are replaced by deuterium.

3. The isolated compound according to claim 1, wherein at least one of $Y^2$ and $Y^3$ is independently deuterium.

4. The isolated compound according to claim 1, wherein both $Y^2$ and $Y^3$ are deuterium.

5. The isolated compound according to claim 1, wherein the compound is selected from any one of:

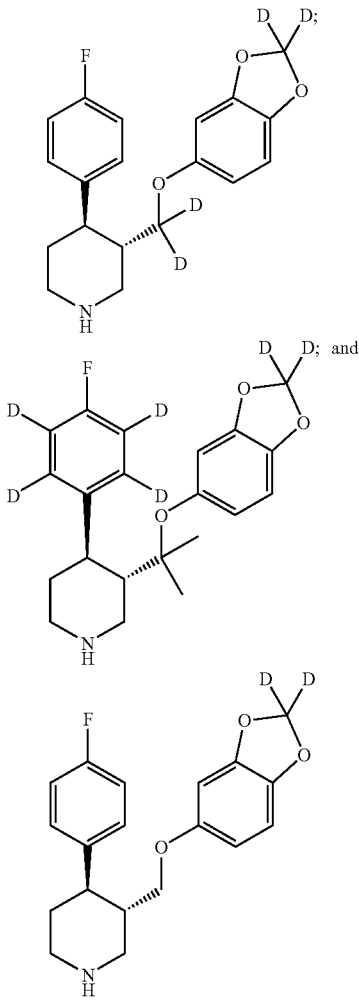

or a pharmaceutically acceptable salt thereof.

6. The compound of claim 5, wherein all hydrogen atoms are present at their natural isotopic abundance.

* * * * *

UNITED STATES PATENT AND TRADEMARK OFFICE
CERTIFICATE OF CORRECTION

| | | |
|---|---|---|
| PATENT NO. | : 8,450,492 B2 | Page 1 of 1 |
| APPLICATION NO. | : 12/688466 | |
| DATED | : May 28, 2013 | |
| INVENTOR(S) | : Roger Tung | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 514 days.

Signed and Sealed this
Tenth Day of December, 2013

Margaret A. Focarino
*Commissioner for Patents of the United States Patent and Trademark Office*